ovided.

United States Patent
Joshi

(12) United States Patent
(10) Patent No.: US 10,350,322 B2
(45) Date of Patent: *Jul. 16, 2019

(54) URINAL AIR FRESHENER

(71) Applicant: Microlin, LLC

(72) Inventor: Ashok V. Joshi, Salt Lake City, UT (US)

(73) Assignee: Microlin, LLC, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/953,400

(22) Filed: Apr. 13, 2018

(65) Prior Publication Data

US 2018/0272022 A1    Sep. 27, 2018

Related U.S. Application Data

(63) Continuation-in-part of application No. 15/413,233, filed on Jan. 23, 2017, which is a continuation-in-part (Continued)

(51) Int. Cl.
*C11D 3/00* (2006.01)
*E03D 9/00* (2006.01)
(Continued)

(52) U.S. Cl.
CPC .... *A61L 9/05* (2013.01); *A61L 9/01* (2013.01); *A61L 9/014* (2013.01); *A61L 9/042* (2013.01);
(Continued)

(58) Field of Classification Search
CPC .. A61L 9/01; A61L 9/014; A61L 9/042; A61L 9/046; A61L 9/05; A61L 9/12;
(Continued)

(56) References Cited

U.S. PATENT DOCUMENTS 5,139,864 A    8/1992   Lindauer
5,336,424 A    8/1994   Van Vlahakis et al.
(Continued)

FOREIGN PATENT DOCUMENTS

CN    203531108 U    4/2014

OTHER PUBLICATIONS

International Search Report and Written Opinion of the International Searching Authority, PCT/US16/41007, dated Sep. 16, 2016.

*Primary Examiner* — Tuan N Nguyen
(74) *Attorney, Agent, or Firm* — Brian C. Trask

(57) ABSTRACT

An automatic dispensing device for volatile fluid operable to apply one or more agent to a local environment for more than 14 days. Preferred devices dispense a first agent for air freshening, and may optionally dispense a second agent, such as a drain cleaner. A workable drain cleaner is structured to permit a slow release of drain cleaning agent. A dispensing device may nonexclusively operate by evaporation of volatile fluid from a polymer or rubber-like carrier material that is infused with the volatile fluid; gravity-induced drip from a bulk supply of volatile fluid through a small orifice onto an emanator; osmotic transfer of volatile fluid from a bulk supply; gas-pump drive of volatile fluid at controlled pressure; or diffusion of volatile fluid through a wall of a container of bulk volatile fluid; and combinations thereof.

20 Claims, 23 Drawing Sheets

Related U.S. Application Data of application No. PCT/US2016/041007, filed on Jul. 5, 2016, which is a continuation-in-part of application No. 14/792,332, filed on Jul. 6, 2015, now Pat. No. 10,105,462.

(51) Int. Cl.

| | | |
|---|---|---|
| *C11D 17/00* | (2006.01) | |
| *C11D 17/04* | (2006.01) | |
| *C11D 3/386* | (2006.01) | |
| *E03D 13/00* | (2006.01) | |
| *A61L 9/01* | (2006.01) | |
| *A61L 9/04* | (2006.01) | |
| *A61L 9/05* | (2006.01) | |
| *A61L 9/12* | (2006.01) | |
| *A61L 9/014* | (2006.01) | |

(52) U.S. Cl.
CPC ............... *A61L 9/046* (2013.01); *A61L 9/12* (2013.01); *C11D 3/0068* (2013.01); *C11D 3/386* (2013.01); *C11D 17/0056* (2013.01); *C11D 17/041* (2013.01); *E03D 9/00* (2013.01); *E03D 9/007* (2013.01); *E03D 13/005* (2013.01); *A61L 2209/133* (2013.01)

(58) Field of Classification Search
CPC .......... A61L 9/127; E03D 9/00; E03D 9/007; E03D 13/005; C11D 3/386; C11D 3/0063; C11D 17/0056
USPC ............................................................. 4/309
See application file for complete search history.

(56) References Cited

U.S. PATENT DOCUMENTS

| | | | |
|---|---|---|---|
| 5,774,905 A | * | 7/1998 | Wager .................. E03D 13/005 |
| | | | 4/309 |
| 5,813,058 A | | 9/1998 | Quigley et al. |
| 8,007,707 B1 | | 8/2011 | Brown et al. |
| 9,234,338 B2 | | 1/2016 | Irwin et al. |
| 2004/0037792 A1 | | 2/2004 | Hiramoto et al. |
| 2005/0148479 A1 | | 7/2005 | Barthel et al. |
| 2013/0031708 A1 | | 2/2013 | Sensel |
| 2014/0075663 A1 | | 3/2014 | Irwin et al. |
| 2014/0259344 A1 | | 9/2014 | Muderlak et al. |
| 2015/0069088 A1 | | 3/2015 | Olson et al. |

\* cited by examiner

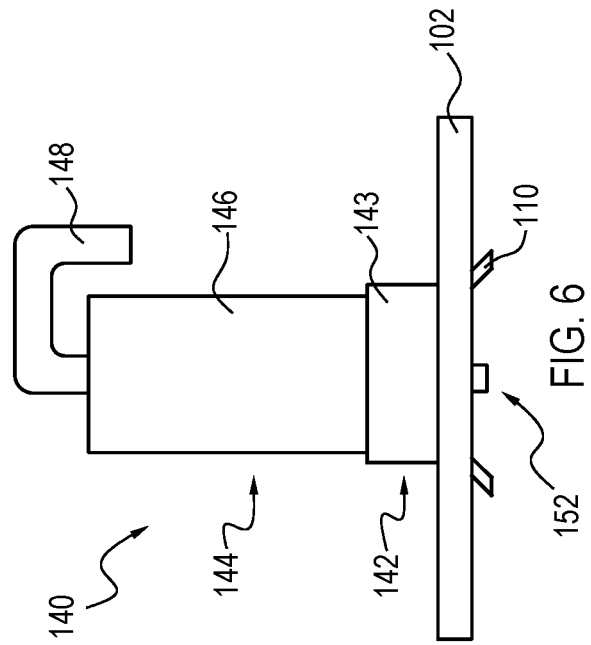
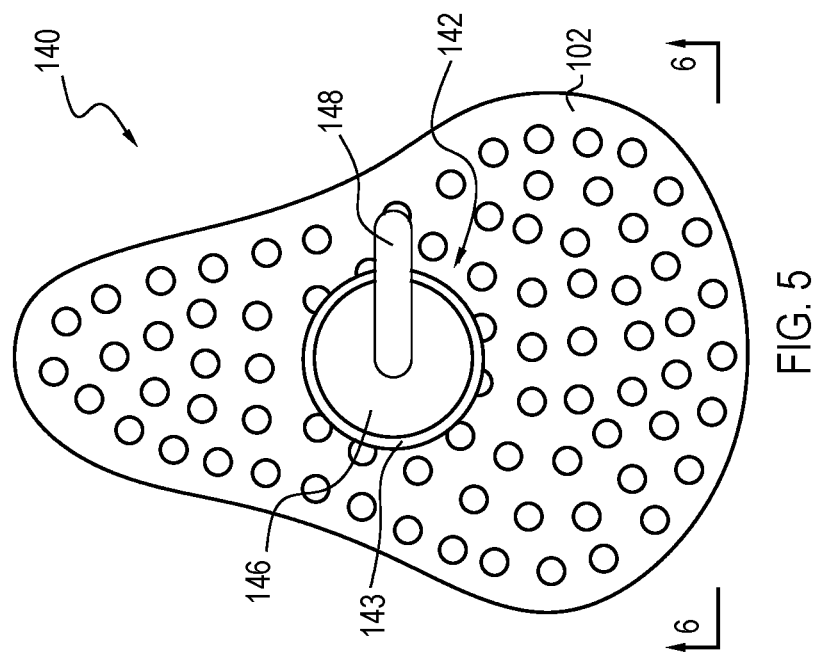

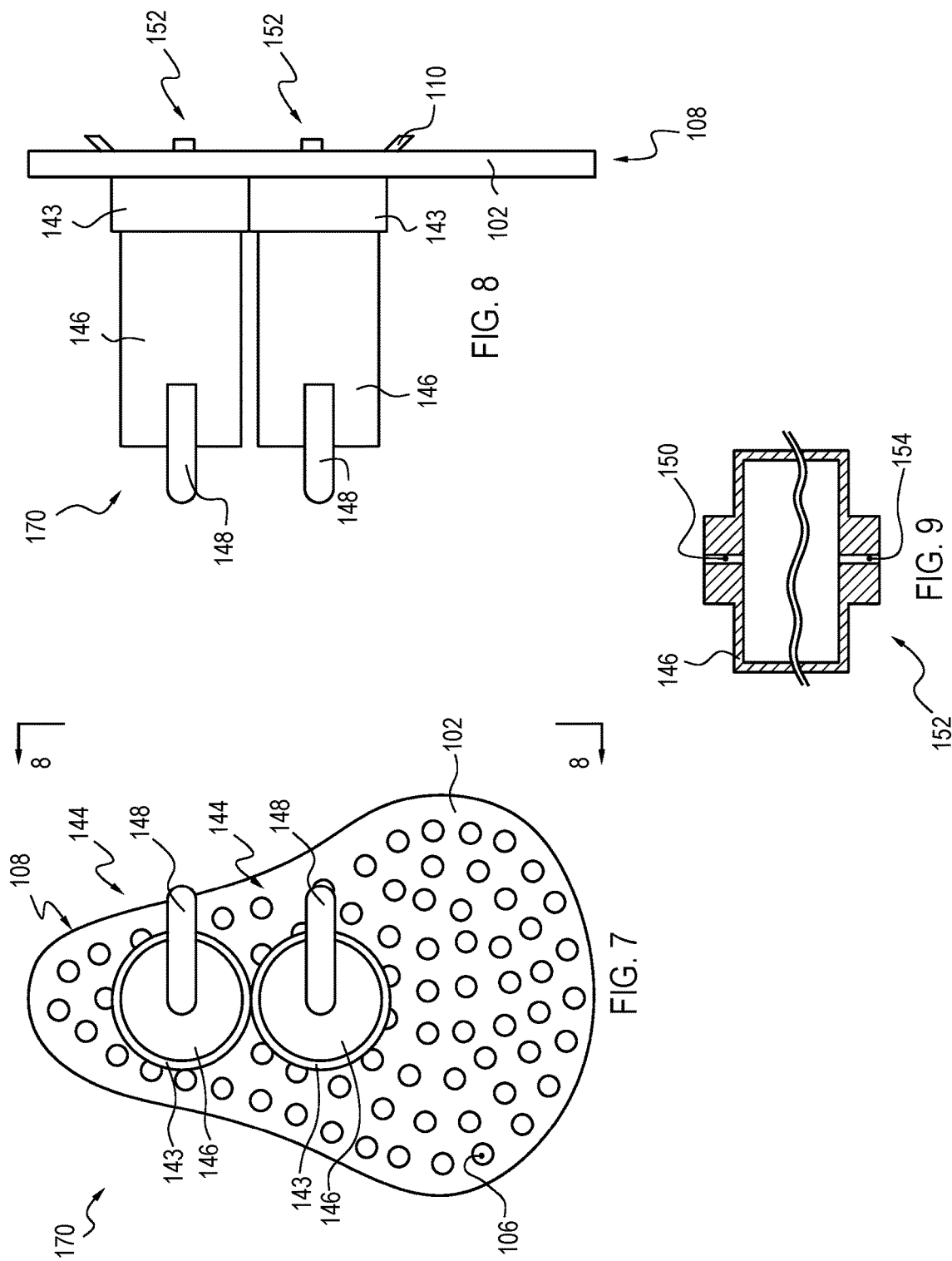

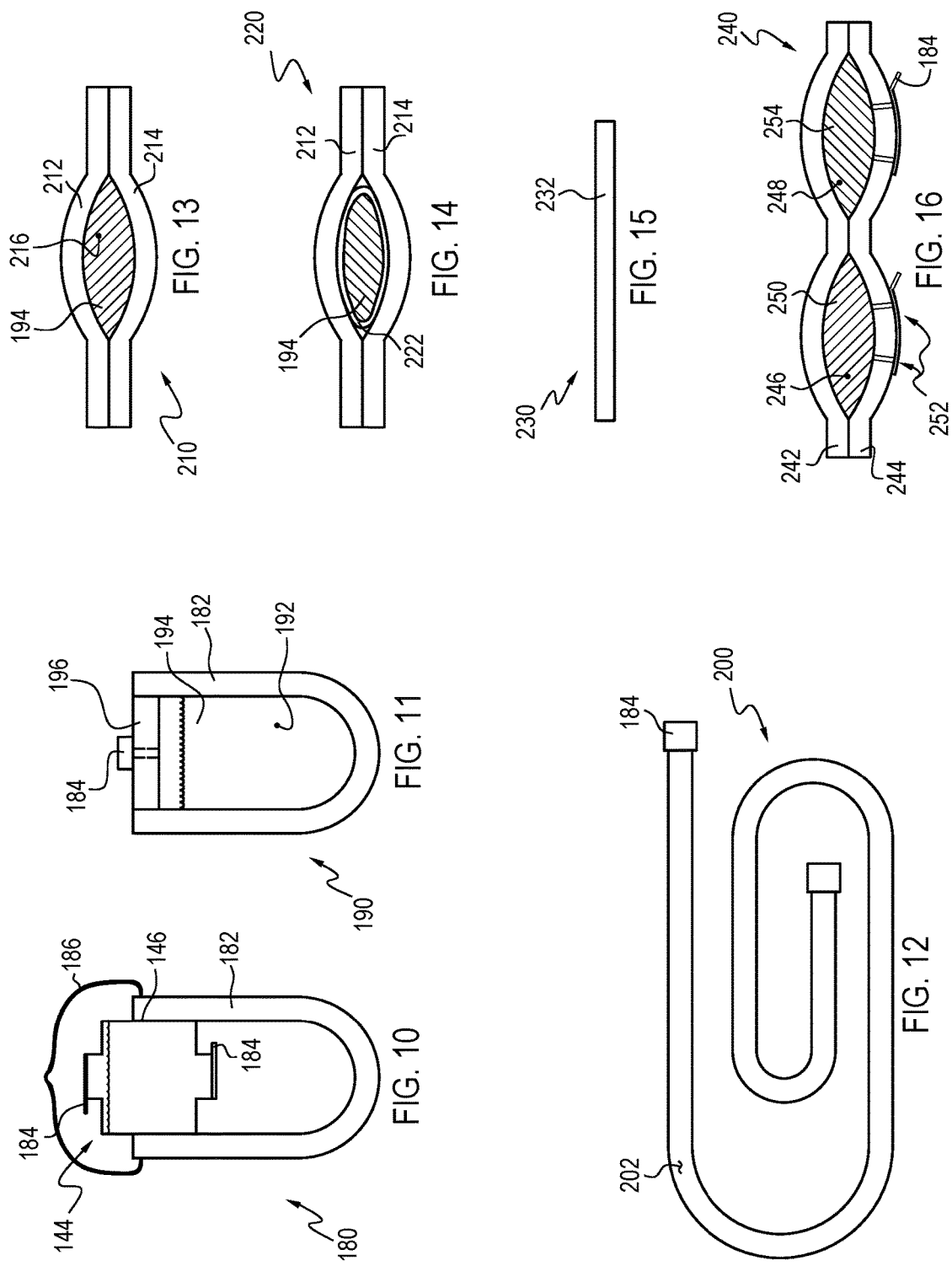

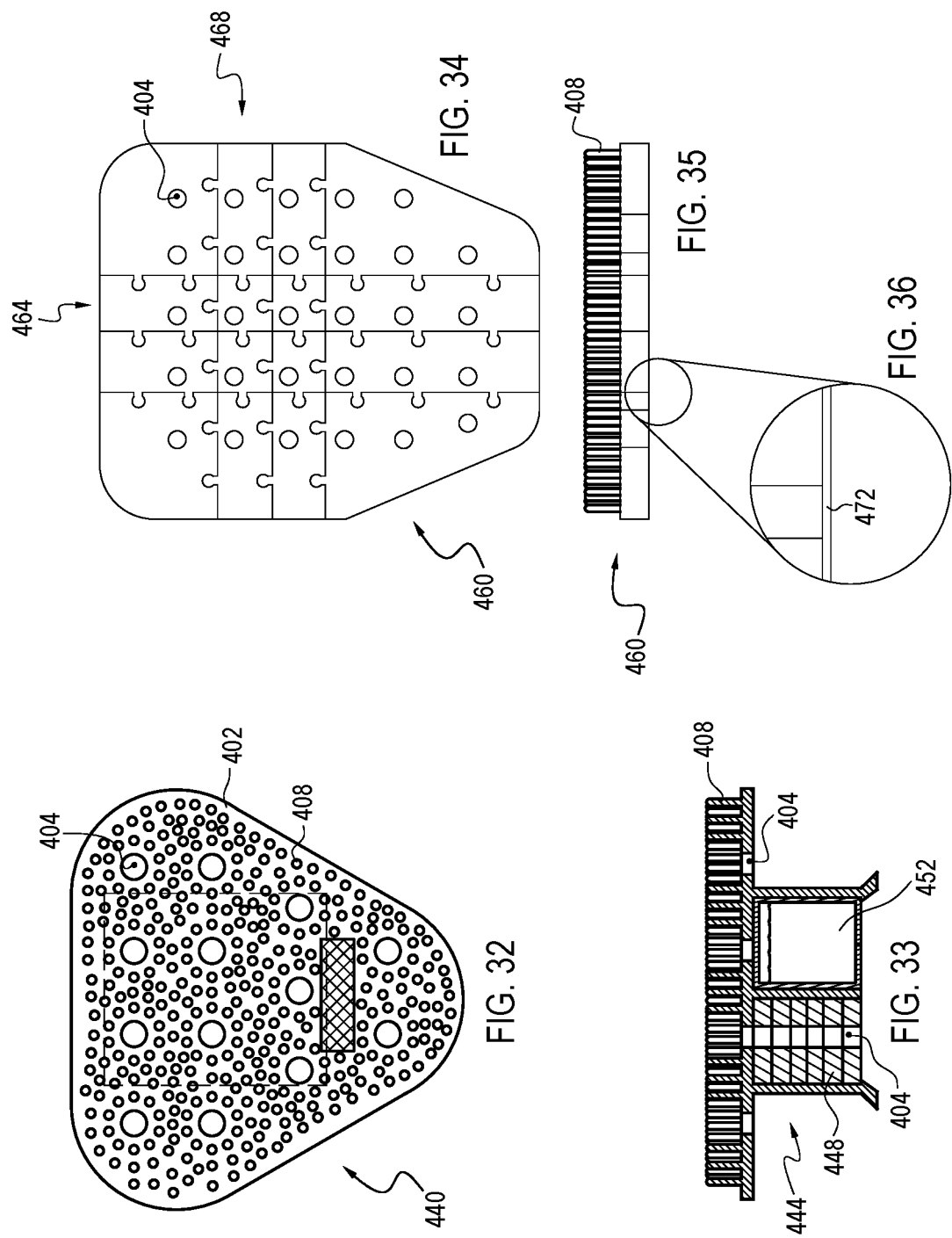

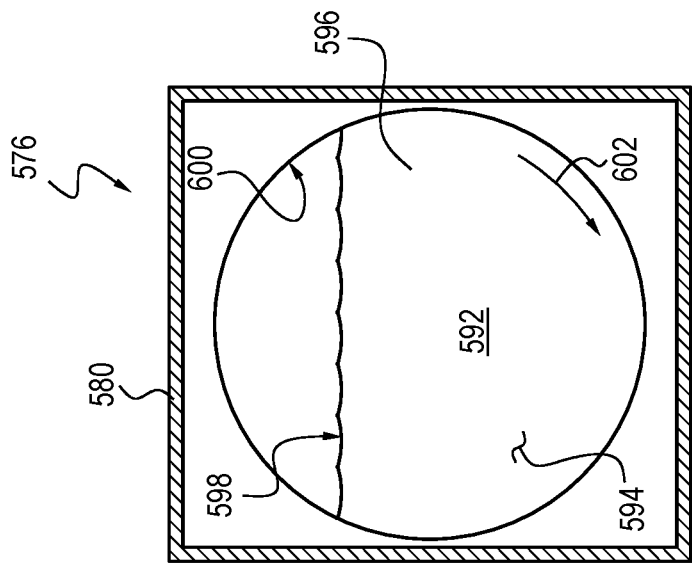
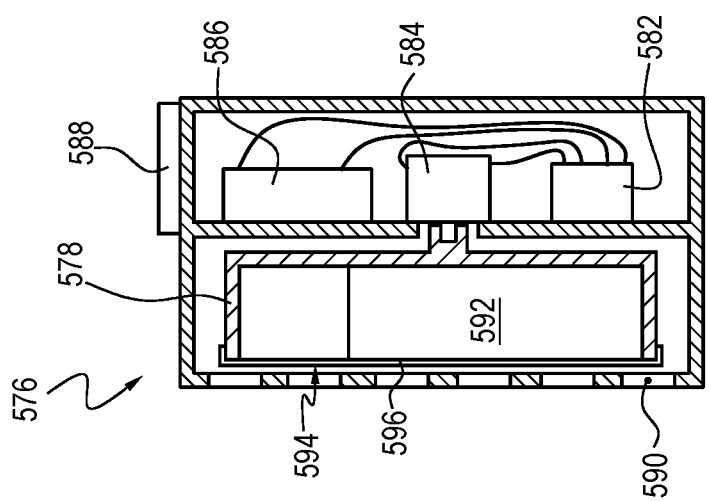
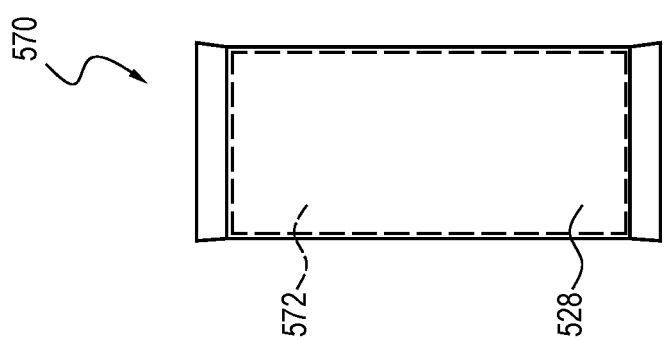

URINAL AIR FRESHENER

PRIORITY CLAIM

This application is a continuation-in-part of the U.S. patent application Ser. No. 15/413,233, titled "HIGH SURFACE AREA RESERVOIR FOR VOLATILE FLUID DISPENSER", filed Jan. 23, 2017, which is a continuation-in-part of the International Application identified under Serial No. PCT/US2016/041007, titled "AIR FRESHENER WITH OPTIONAL DRAIN CLEANER" with an International filing date of Jul. 5, 2016, which is a continuation-in-part of U.S. patent application Ser. No. 14/792,332, filed Jul. 6, 2015, for AIR FRESHENER WITH OPTIONAL DRAIN CLEANER, the entire contents of all of which are incorporated by this reference as though set forth herein in their entirety.

BACKGROUND

Technical Field

This invention relates generally to dispensers for volatile fluids, such as products for air freshening, mosquito abatement, and/or drain cleaning, and their use.

Background

Air freshening, and/or masking of unpleasant odors, is commonly done in certain enclosed environments, such as bathrooms and automobiles. A typical air treatment includes introduction of a masking fragrance, or scent, into the environment. Known devices for introducing a scent or fragrance into the environment on-demand include aerosols, which may be hand operated when a need is detected.

Some air freshening devices may automatically dose the environment over a desirable period of time. Certain such devices require an additional source of energy, such as devices that are plugged into an electrical outlet to operate a warming element. Other devices are structured to off-gas, or sublimate, under the ambient conditions of the environment in which they are deployed. One such device includes a puck of mothball-like material that can be placed into a urinal. Another air freshener includes a fragrance-soaked ornament that is structured to hang on a rear view mirror of an automobile. Typically, such a device produces an initially strong fragrance that steadily diminishes over time.

Introduction of scent may also be performed during certain processing operations, such as when drying articles of clothing in a mechanical clothes drier. For example, it is known to include scent as a dry component carried on a disposable sheet of substrate that also is structured to reduce build-up of static electricity.

It would be an improvement to provide an air freshening material and device that can dispense scent to an environment automatically over a period of time in excess of about 14 days without requiring an additional energy source, and optionally provide an additional function, such as drain cleaning. Desirably, the improved air-freshening device will produce a substantially constant level of detectable fragrance in the environment over the desired time increment.

DISCLOSURE OF THE INVENTION

Embodiments may be characterized as distribution devices to provide long-term release of one or more volatile agent into a local environment. Certain embodiments structured according to principles of this invention provide an automatic air freshener for use over a period of time in excess of about 14 days. A preferred embodiment includes a container that is associated with an air freshener to provide an additional function, such as drain cleaning.

A workable air freshener includes an emanator that may be formed from a material selected from the group including styrene-based polymer, styrene-based rubber, ethylene propylene diene monomer (EPDM), thermoplastic polyurethane (TPU), butadiene-based polymer, butadiene-based rubber, gum rubber, and cellulosic rubber, other elastomer, rubber, or plastic material that can imbibe volatile fluid, and the like sorts of materials, and including combinations thereof, or an adsorbent material having high-surface area greater than about $10 \text{ m}^2/\text{g}$, or an absorbent material including cellulose or polymer sponge, and the like. A currently preferred emanator is injection molded in final form as a unitary element.

A scented or other volatile fluid is typically dispersed, loaded, or otherwise imbibed into the emanator to a weight percent of between about 3% and about 400%, where weight percent is calculated as A/B*100, and A is weight of volatile fluid and B is weight of emanator material. The air freshener may be loaded with volatile fluid by wetting the emanator with a volatile fluid under ambient temperature conditions and for a period of time between about one hour and about seven days. For purpose of this disclosure, ambient temperature conditions means the fluid is simply placed into a container in a room, and the air temperature of the room is maintained between about 50° F. and about 100° F. Operable volatile fluids include various scent-emitting oils, mosquito repellant, and the like.

An emanator typically applies a vaporized agent to the local environment. An agent may be a scent, or mosquito repellant, air care product, medicinal fluid, or some other volatile element of which vapor application to the local environment is desired.

A workable emanator may be formed by causing volatile fluid to be loaded, dispersed, absorbed, adsorbed, or otherwise imbibed into a carrier material (e.g., styrene-based, butadiene-based, or an adsorbent material having high-surface area greater than about $10 \text{ m}^2/\text{g}$), and/or an absorbent material, or combinations thereof, to a weight percent of greater than about 3%, 5%, 10%, 20%, 30%, or more. Subsequent to being loaded into the carrier material, the volatile fluid may slowly evaporate from a surface of the carrier material to dispense volatile fluid vapors to the local environment. An emanator may include a volatile fluid that is dispersed into a carrier material to a weight percent of between about 3%, 10%, 20%, 30%, etc., and up to about 150%, 200%, 300%, 400%, or more. An alternative emanator may simply provide a surface from which a volatile fluid may evaporate. In some case, an emanator may be wetted by drop-wise distribution of volatile fluid from a container onto the emanator. In other cases, an emanator may be a portion of the container of volatile fluid, and fluid may diffuse through the emanator from a container-side to an evaporation-side.

A workable embodiment according to certain aspects of the invention has a carrier material to hold a quantity of volatile fluid, and a volatile fluid dispersed into the carrier material. A currently preferred carrier material includes an adsorbent material having a surface area greater than 10 $\text{m}^2/\text{g}$. Typically, the volatile fluid is loaded into the adsorbent carrier material to a weight percent of between about 5% and about 200%, where weight percent is calculated as A/B*100, and A is weight of volatile fluid and B is weight of adsorbent material.

An embodiment may include an emanator with a wicking and distributing wall disposed and structured to provide a surface area from which volatile fluid may evaporate into a local environment. An embodiment may include a container structured to hold the carrier material and to permit egress of volatile fluid vapor from the adsorbent material into the local environment. Sometimes, a container is structured to hold the carrier material and to permit egress of volatile fluid vapor from the carrier material into the local environment. However, carrier material may form a stand-alone device. In certain cases, the container and the emanator may be structured in harmony such that the container defines a portion of the shape of the emanator.

A workable adsorbent material includes a material selected from the group consisting of high-surface area ceramic, Alumina, γ-form Alumina, Silica, activated carbon, carbon black, molecular sieves, and zeolite. An adsorbent material may be arranged in the form of a plurality of beads, powder, meal, or in any desired shape.

The carrier material for an emanator may include an adsorbent constituent material, and/or an absorbent constituent material. A carrier material can sometimes be in the form of dough. One workable dough includes an adsorbent material component in powder or meal form, with the adsorbent constituent material having a surface area of greater than about 200 $m^2/g$. For example, adsorbent material and absorbent material may initially be in powder or meal form, and can be mixed together with a volatile fluid to form dough.

Sometimes, a carrier material further includes hydrophobic material arranged to reduce a rate of discharge of volatile vapor from the carrier material to a local environment responsive to moisture-induced off-gassing of volatile fluid. That is, moisture can be imbibed from a moist environment into the carrier material to displace volatile fluid, thereby increasing a rate of volatile fluid discharge from the carrier material. Hydrophobic material to reduce fluid or moisture uptake into a carrier material may be provided as an exterior coating, or may be adsorbed into the carrier material. Sometimes, a gas-generating compound may also be included in an air freshener carrier material to increase the rate of off-gassing of volatile fluid responsive to uptake of moisture from the local environment.

One embodiment includes adsorbent material in the form of a plurality of beads, and absorbent material in the form of a slab configured to form a wall. Volatile fluid is infused into the adsorbent and absorbent materials. The wall is disposed as a divider to form compartments inside a skeleton, and adsorbent beads are disposed in the compartments. The skeleton provides a perimeter including a plurality of apertures through which vapor from the carrier material may propagate into the local environment. In a preferred embodiment, the wall comprises a cellulose sponge. The skeleton may be configured as an elongate tube having a round, triangular, rectangular, or otherwise shaped cross-section. In a preferred case, the slab of absorbent material is configured as a cap of the tube, and a slab of absorbent material is disposed as a floor of the tube.

In one embodiment, the carrier material includes a plurality of spherical beads, and the beads are carried on a dish structured for disposition in a bowl of a urinal. An embodiment may further include one or more color-changing element to indicate remaining life of the apparatus. An embodiment may include structure adapted to release a drain cleaning agent over the life of the apparatus.

An embodiment of an air freshener, or generally, a dispenser of volatile fluid, may include a body with an absorbent material and a volatile fluid absorbed in the body. An exterior coating (such as a hydrophobic material) may be applied on the body to reduce a rate of discharge of volatile fluid from the body to a humid or wet local environment. Also, a gas-generating element may be disposed inside the coating to increase a rate of discharge of volatile fluid vapor from the body to the local environment responsive to migration of water molecules through the coating and into the body. An exterior coating or other rate-reducing material may be selected in harmony with a gas-generating compound to balance rate of discharge of a volatile fluid into a service environment for purpose of air freshening.

A dispenser of volatile fluid may include an emanator comprising an adsorbent carrier material having a surface area greater than 200 $m^2/g$ and a fragrant oil dispersed into the adsorbent material to a weight percent of greater than about 5%, where weight percent is calculated as A/B*100, and A is weight of the adsorbed volatile fluid and B is dry weight of adsorbent material.

The invention may be embodied in a device for, and/or a method for making, an air freshener. One exemplary method includes providing an emanator in final-form. Preferably, the emanator is structured to resist a humanly perceptible change in configuration size and shape from the final-form during a useful life of the emanator for air freshening. A workable emanator may be formed from a material capable of imbibing a volatile fluid when exposed to the volatile fluid in a liquid environment and subsequently off-gassing the imbibed volatile fluid when exposed to a gas environment. The method further includes wetting the emanator with a volatile fluid under ambient temperature conditions for between about 1 hour and about 48 hours to disperse a fragrant oil into the emanator to a weight percent of greater than about 3%, where weight percent is calculated as A/B*100, and A is weight of imbibed volatile fluid and B is weight of the emanator material prior to the imbibing process.

An emanator may imbibe or otherwise uptake volatile fluid during exposure of the emanator material to any operable saturating fluid environment, including dipping in bulk fluid or spray application of volatile fluid onto emanator material. An emanator may simply be wetted or soaked in volatile fluid for any period of time between about one hour and about 24 hours, or even up to several days. In a preferred method, the emanator is bathed in volatile fluid for a period of time between about 4 hours and about 24 hours, with workable time periods being consecutively longer by about 1 minute increments. That is, a workable time period may be 1 hour; or 1 hour, 1 minute; or 1 hour, 2 minutes; etc.

In a preferred arrangement, the emanator is structured as a unitary element from a material selected from the group consisting of styrene-based polymer, styrene-based rubber, ethylene propylene diene monomer (EPDM), thermoplastic polyurethane (TPU), butadiene-based polymer, butadiene-based rubber, gum rubber, and cellulosic rubber, or combinations there-of. The emanator may be structured as a unitary element from a material selected from the group consisting of styrene-based rubber, ethylene propylene diene monomer (EPDM), thermoplastic polyurethane (TPU), butadiene-based rubber, and cellulosic rubber. In some cases, the emanator is injection molded.

In one embodiment, the emanator includes a shell with a top surface spaced apart from a bottom surface by a substantially uniform distance or thickness. A rim of the shell may be configured to provide a support foot disposed around a portion of a perimeter of the shell to support the shell on a surface during use. A preferred shell includes a cross-section having an arcuate shape to define a volume bounded in part by the bottom surface and being open to permit access to the volume through an opening bounded by the perimeter. Desirably, the top surface carries a plurality of upstanding splash knock-down structures for particular application to services as a urinal screen. In that case, the shell includes a plurality of penetrations structured to permit fluid to travel through the shell.

Sometimes, the shell's bottom surface is structured to permit attachment of a container there-to. A method may further include attaching a container to depend from the bottom surface. A workable container is porous to permit travel of fluid there-through. A method may further include placing a first quantity of drain cleaning compound into the container prior to attaching the container to the bottom surface. It is desirable for the container to be structured in harmony with the emanator to permit the container to be installed in registration with the emanator in a tool-free operation. A method may further include installing the container in registration with the bottom surface prior to placing the emanator in service to freshen air. It is also desirable for the container to be structured in harmony with the emanator to permit the container to be removed from registration with the emanator in a tool-free operation. A method may further include removing the container from registration with the bottom surface, refilling the container with a quantity of drain cleaning compound, and re-installing the container in registration with the bottom surface prior to again placing the emanator in service to freshen air.

One purpose of an emanator is to release volatile fluid into a local environment. Materials that are useful to form a workable emanator may be characterized in many ways. For example, operable materials may be selected from generally recognized material classifications such as rubber, polymer, high-surface area, and the like. Embodiments may further be specified by more detailed material or chemical composition, such as styrene-based, butadiene-based, high-surface area, and the like.

An emanator may be, or directly or indirectly provide, a storage system for the volatile fluid. Certain operable emanating materials may be characterized by a principle of operation under which fluid flows into or through the material for initial storage and/or subsequent release to the environment. For examples, fundamental principles of operation that can cause an effect on fluid flow nonexclusively include adsorption, absorption, capillary action, gravity, adhesion, diffusion, and molecular disruption or combination. Certain materials that may be employed to form an emanator have a theoretical density of greater than 90%.

Certain operable emanators may be formed from materials that have a melting point that is greater than about 200° F., 300° F., 400° F., 500° F., 600° F., 1000° F., 1500° F., 2000° F., or more. While an emanator may never be placed into service in a high temperature environment, the melting point of a candidate emanator material may provide a distinction over other materials that are not encompassed within certain embodiments.

BRIEF DESCRIPTION OF THE DRAWINGS

In the drawings, which illustrate what are currently considered to be the best modes for carrying out the invention:

FIG. 5 is a plan view of another embodiment according to certain principles of the invention;

FIG. 6 is a side view of the embodiment in FIG. 5, looking in the direction of the arrows 6-6;

FIG. 7 is a plan view of another embodiment according to certain principles of the invention;

FIG. 8 is a side view of the embodiment in FIG. 7, looking in the direction of the arrows 8-8;

FIG. 9 is a cross-section view of top and bottom portions of a container to accomplish a gravity-assisted release of fluid operable in certain embodiments of the invention;

FIG. 10 is a view in elevation, partially in cross-section of another embodiment according to certain principles of the invention;

FIG. 11 is a view in elevation, partially in cross-section of another embodiment according to certain principles of the invention;

FIG. 12 is a plan view of another embodiment according to certain principles of the invention;

FIG. 13 is a cross-section view of another embodiment according to certain principles of the invention;

FIG. 14 is a cross-section view of another embodiment according to certain principles of the invention;

FIG. 15 is a side view of another embodiment according to certain principles of the invention;

FIG. 16 is a cross-section view of another embodiment according to certain principles of the invention;

FIG. 32 is a plan view of an air freshener structured for use as a urinal screen;

FIG. 33 is a cross-section view taken at section 33-33 in FIG. 32;

FIG. 34 is a plan view of an air freshener structured for use as a size-adjustable urinal screen;

FIG. 35 is an end view of the embodiment in FIG. 34;

FIG. 36 is a close-up view of a portion of the embodiment in FIG. 35;

FIG. 43 is a plan view of an alternative embodiment;

FIG. 44 is a plan view of an alternative embodiment;

FIG. 45 is a side view in partial cross-section of the embodiment in FIG. 44;

MODES FOR CARRYING OUT THE INVENTION

Figure 1:
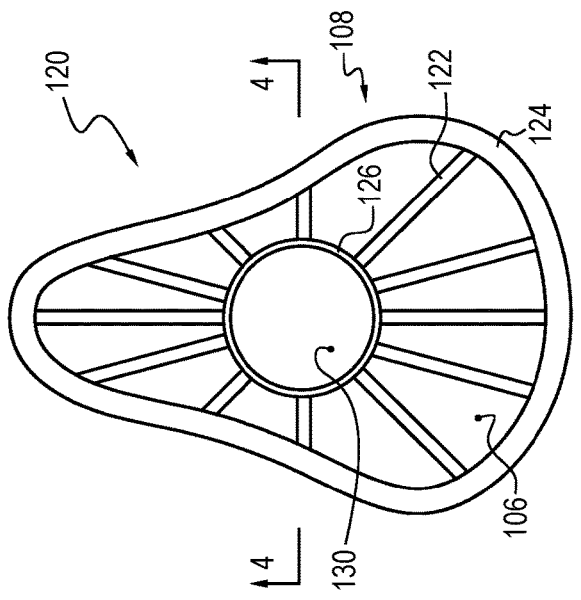
FIG. 1 is a plan view of an embodiment according to certain principles of the invention.
Figure 2:
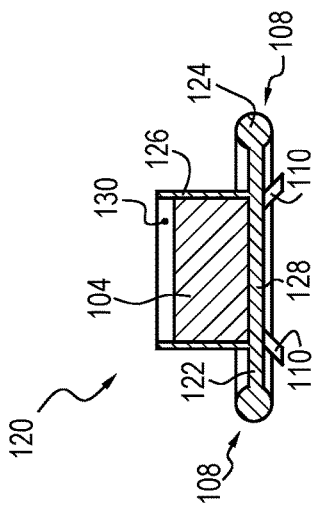
FIG. 2 is a side view of the embodiment in FIG. 1.

A first embodiment of a dispensing device operable as an air freshener according to certain principles of the invention is illustrated in FIGS. 1 and 2, and generally indicated at 100. Air freshener 100 is particularly adapted for deployment in a urinal. It should be appreciated that alternative embodiments of the invention are not limited to such use. The air freshener 100 and other embodiments described below serve as simple examples to illustrate certain elements.

Air freshener 100 includes a screen 102 substrate, which may be considered a container, or sometimes a support, in that the screen 102 carries a quantity of air fresher material 104. The preferred air freshener material 104 is a scent-bearing styrene-based material manufactured from styrene-based polymers or styrene-based rubbers, as will be described in detail below. One way to obtain the illustrated embodiment 100 is to simply coat the screen 102 with a glue-like mixture of air freshener material 104. Alternatively, it is within contemplation to mold or bond air freshener material 104 onto a substrate 102, or even to form the entire air freshener 100 by molding air freshener material 104 and thereby reduce the number of constituent elements.

A plurality of apertures 106 permit fluid to pass through the air freshener 100, in conventional manner. Typically, the air freshener 100 is placed into a urinal and contacts the bowel around portion(s) of the perimeter 108. Sometimes, one or more optional foot 110, or other operably-shaped protrusion from the screen 102, may be included to better hold the air freshener 100 in a desired position.

Certain embodiments may include provisions to reduce splash of a fluid stream from part of a device, such as an embodiment 100, 120, 350, or 460, (see also FIGS. 4, 23, 36, etc.), including a rubber or plastic or other generally hydrophobic exterior surface. For example, it is within contemplation to coat part of a device, such as surface 112, with a surfactant material. In an alternative construction, the surface 112 may also or alternatively be treated by corona or electrical plasma to convert a generally hydrophobic material surface to a more hydrophilic surface. As illustrated in FIGS. 1 and 2, plasma radiation, generally indicated at 114, from a plasma radiation source 116 may be applied to a plastic or rubber surface 112, or to a surface that is made from some other generally hydrophobic material.

An air freshener according to certain principles of the invention, such as air freshener 100, will produce an air freshening scent at a substantially constant level for a period in excess of about 14 days from time of first deployment. In this case, the term "substantially constant level" means that a qualitative standard is employed, and a person in proximity to the device will notice an appreciable odor or scent-emanation from the air freshener 100 for at least about 14 days from first deployment of the air freshener 100 in its use environment. Desirably, the scent will remain at a humanly-perceptible or detectable and operable level for a greater period of time, such as in excess of about 30 days, 60 days, 90 days, or sometimes even longer.

Figure 3:
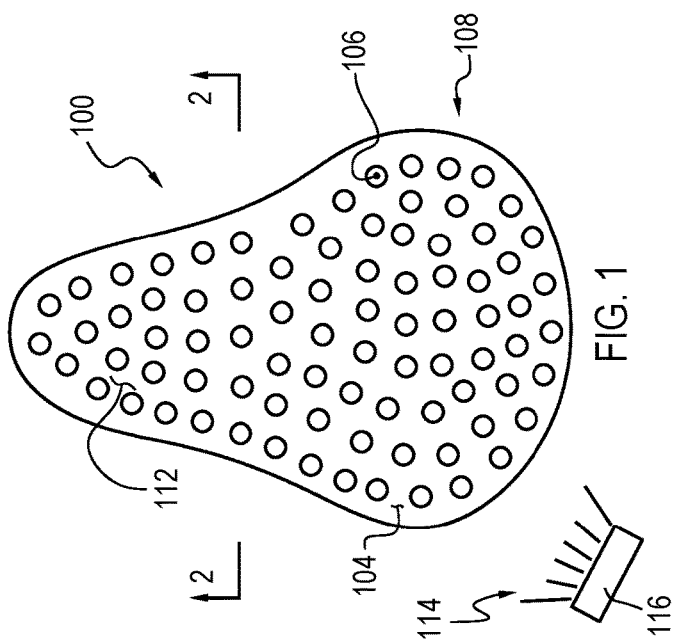
FIG. 3 is a plan view of another embodiment according to certain principles of the invention.
Figure 4:
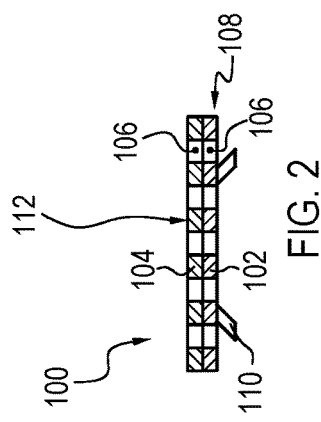
FIG. 4 is a cross-section view of the embodiment in FIG. 3, taken at section 4-4 and looking in the direction of the arrows.

A second embodiment of a dispensing device operable as an air freshener is indicated generally at 120 in FIGS. 3 and 4. A plurality of spokes 122 extend between the rim 124 and an interior wall 126 to define apertures 106. The wall 126, in combination with floor 128, defines a compartment, vessel, or container 130, in which is received a quantity of volatile air freshener material or fluid 104. The compartment 130 is structured to permit scent to emanate from the material 104 to the local environment in which the device 120 is deployed. In this embodiment 120, air freshener material 104 may run the gamut from a flowable glue-like substance, to a solid puck or brick-like element, depending on user preference and manufacturing process used to form the air freshening material. Additional details of operable air freshener materials 104 are set forth below, partially in connection with a description of FIGS. 17 and 18. Typically, a portion of perimeter 108 rests against the bowel of the urinal in which the device 120 is deployed. Again, one or more optional foot 110, or other operable extension member, may sometimes be provided to facilitate holding the device 120 in a desired position.

FIGS. 5 and 6 illustrate a third embodiment of dispensing device structured as an air freshener, generally 140, according to certain principles of the invention. Air freshener 140 includes a screen 102 that carries holding structure, generally 142, that is configured and arranged to hold a dispenser of fluid, generally 144, in an operable position. One workable holding structure 142 includes circumscribing wall 143. A currently preferred dispenser of fluid 144 includes the illustrated container 146, which is structured to provide a gravity-assisted, drop-wise release of fluid from a bulk quantity confined inside the container 146. For use as an air freshener, the bulk fluid confined inside container 146 is typically a fragrance of some sort, such as a fragrant oil. In other applications, a bulk fluid sometimes may simply be a volatile oil or other fluid (which may, or may not, be volatile). In one alternative construction that is loosely based upon FIGS. 5 and 6, an air freshening material may be carried on screen 102, and the fluid inside container 146 may be a liquid drain cleaner.

During use in a urinal application, container 146 typically includes a splash guard, such as tube 148, structured to resist fluid flow into the top vent aperture 150 (see also FIG. 9). A workable splash guard may be alternatively structured, including as an umbrella or mushroom providing a shield extending over the vent aperture 150. Container 146 has a discharge end, generally 152, disposed to release fluid through a discharge aperture 154 (see FIG. 9).

An operable dispenser of fluid 144 is capable of releasing fluid at a controlled, substantially constant rate over a period of time in excess of about 14 days, preferably in excess of about 30 day, or so. As used herein, the term "substantially constant rate" means a qualitative standard is employed. In rigorous terms, a quantitative change in flow rate of 20%, 30%, 50%, or even 100% may be considered "substantially constant", depending upon the application For air-freshening purpose, the more important effect is accomplishing a humanly-perceptible substantially constant air freshening smell. In application as a drain cleaner, the important effect is accomplishing reliable release of sufficient fluid to maintain drain cleanliness over the desired time increment.

One workable fluid dispenser 144 operates under principles of gravity-induced drip from a bulk supply of fluid through a small orifice. Certain details of construction and operation of such a dispenser 144 are disclosed in U.S. Provisional patent application No. 62/164,650. A second workable fluid dispenser 144 operates under principles of osmotic transfer of fluid from a bulk supply. Certain details of construction and operation of that type of dispenser 144 are set forth in U.S. Pat. No. 8,240,261. A third workable fluid dispenser 144 operates under principles of gas-cell drive of fluid at substantially controlled pressure. Certain details of construction and operation of that third type of dispenser 144 are set forth in U.S. Pat. Nos. 6,823,383; 6,957,779; and 8,939,435. The entire disclosures of the patent documents mentioned in this paragraph are hereby incorporated as though set forth herein in their entirety.

FIGS. 7 through 9 illustrate certain details of construction of a fourth 'type' of embodiment of a dispensing device, generally indicated at 170, structured according to certain principles of the invention. The illustrated embodiment 170 includes two fluid dispensers 144 carried on a support or screen 102. In the particular embodiment illustrated in FIGS. 1 and 8, the fluid dispensers 144 are of the gravity-induced drip type 146. One container 146 is typically used to dispense fragrance, and the other container 146 is typically used to dispense drain cleaner. Other types of fluid dispensers 144 may be employed, and may be combined in more than one type and number. It is also within alternative contemplation that a quantity of styrene-based fragrance may be used as the air fresher element, and one or more fluid dispenser 144 may be employed to dispense fluid drain cleaner or other fluid. In the latter case, fragrant material 104 may be applied as a coating to the screen 102, may form the screen/support 102, or may be confined in a compartment, such as a container 130 (FIG. 4) formed by a wall 126 or 143 associated with a screen or support 102.

The embodiment in FIG. 10, and generally indicated at 180, illustrates an alternative type of dispensing device operable as an air freshener. Air freshener 180 includes a fluid dispenser, generally 144, adapted to discharge fluid onto an emanator 182. A currently preferred emanator 182 is formed from, or includes, a styrene-based polymer, styrene-based rubber, or butadiene-based material, and the fluid dispenser 144 discharges a fragrant oil onto the emanator 182.

One workable fluid dispenser 144 includes the illustrated gravity-induced drop type 146. In that case, some sort of seals are desirably provided to confine fluid inside the container 146, e.g. during shipping and handling prior to placing the device 180 into service. A workable seal includes the illustrated ubiquitous tear-off foil cover 184 that is removably bonded to the container 146 and blocks fluid flow from respective vent or discharge openings. Other conventional sealing structures may be used, including stoppers, corks, twist-off threaded caps, and the like. Sometimes, suspension structure, such as a handle or bail 186 may be provided to facilitate placement of a device into operable service as a suspended element. Alternatively, some sort of stand-up support structure, such as a foot (not illustrated), may permit placement of a device 180 in an operable orientation onto a supporting surface, such as a table or the floor.

FIG. 11 illustrates another embodiment of a dispensing device operable as an air freshener, generally 190, that is structured for operation over an extended period of time. An emanator 182 defines at least part of a volume 192, in which an excess quantity of fragrant fluid 194 is stored. A currently preferred emanator 182 includes a material selected from, or includes, a styrene-based polymer, styrene-based rubber, or butadiene-based material, or combinations thereof, and the volatile fluid 194 (typically a fragrant oil) is disposed in direct contact with one side of the emanator 182. A cover or cap 196 may be sealed against undesired fluid flow through a fill-opening by a seal element 184. The fill opening may also operate as a vent to admit volume-replacement air during operational service of the dispensing device 190.

FIG. 12 illustrates an embodiment, generally 200, that is structured to provide an enlarged surface area 202 to provide a more concentrated source of scent over a significant period of time. The emanator of embodiment 200 is formed from a coiled tube with a wall made from a dispensing material through which volatile fluid can travel effective to deploy volatile fluid molecules into the local environment. Volatile fluid molecules may diffuse through, and evaporate from, the external surface of the dispensing material. Operable such dispensing materials non-exclusively include styrene-based polymer, styrene-based rubber, or butadiene-based material, and combinations thereof. Various heat-shrinkable polymeric or nano-porous polymeric materials are also operable as dispensing materials. Similar to embodiment 190, a volatile (e.g., fragrance) fluid is disposed in direct contact with the dispensing material, and may be confined by one or more seal element 184.

The embodiment, generally 210, illustrated in FIG. 13 represents the case where a pocket or space is formed between two layers of plastic-, or rubber-like, or other polymer materials. At least one side of a pocket or void may include styrene-based or butadiene-based material. That is, one or both of top sheet 212 or bottom sheet 214 can be a styrene-based or butadiene-based material, or other material through which volatile fluid molecules may permeate or migrate for application to the local atmosphere. Fragrant or other volatile fluid 194 is placed into the void, pocket, or compartment 216 that is formed between top sheet 212 and bottom sheet 214, and the edges surrounding the void 216 may be sealed. Alternatively, the volatile fluid may be injected into the void 216.

FIG. 14 illustrates an embodiment, generally 220, including a separate and impermeable pouch 222 in which volatile fluid 194 is initially confined. Again, one or both of top sheet 212 or bottom sheet 214 is typically formed from a styrene-based or butadiene-based material, or other material through which volatile fluid molecules may permeate or migrate for application to the local atmosphere. A workable sheet 212, 214 can be manufactured from materials including styrene-based polymers, styrene-based rubbers, EPDM, gum rubber, cellulosic rubber, and other materials that absorb and emanate a fragrant material. A workable pouch 222 can be made from polymeric, plastic, or plastic-like materials that are impermeable to the volatile fluid 194. A user may rupture the pouch 222 to release fluid 194 into contact with the styrene-based or butadiene-based material. That material then operates as an emanator to disperse scent into the environment local to the device 220. A pouch 222 may be ruptured by stepping on the device 220, poking the pouch 222 with a sharp object (desirably making a hole in sheet 212 or 214 too small to leak), or otherwise causing a break in the wall of the pouch 222 through which fluid 194 may escape for contact with the styrene-based or other emanator material.

FIG. 15 illustrates a generalized object made from a carrier material, such as a styrene-based or butadiene-based material, generally indicated at 230. The object 230 can be any sort of 3-dimensional shape. The object 230 is soaked in, or otherwise wetted by, fragrant fluid at a temperature between about 20° C. and about 50° C. for a period of time greater than about 2 hours to form an emanator 232. In such a process, scented or other volatile fluid is dispersed into the material to a weight percent of between about 5% and about 100% to perhaps 200%, where weight percent is calculated as A/B*100, and A is weight of volatile fluid and B is weight of carrier material. In a preferred embodiment, the weight gain of a styrene-based polymer or rubber-like material is about 35%.

For example, the device 230 in FIG. 15 can be a flat section of styrene-based polymer or styrene-based rubber seen in side view. The plan view can be formed to resemble a shape, such as a pine tree, rectangle, or any other desired shape. A logical fragrant or scented volatile fluid for a pine tree shape would include pine-scented fragrant oil. Provision may be made to permit suspending the device 230 from, for non-limiting examples: a rear view mirror in an automobile; or a clothes-rod in a closet.

FIG. 16 illustrates a generalized embodiment, generally 240, of a multi-compartment fluid dispenser. Device 240 can be manufactured by bonding top sheet 242 to bottom sheet 244 around perimeters of void compartments, similar to the embodiments in FIGS. 13 and 14. Multiple compartments can be made, similar to bubble wrap. The illustrated embodiment 240 includes two compartments, namely compartment 246 and compartment 248. Top and bottom sheets 242, 244 may conveniently be manufactured from polymer sheets, including plastic, rubber, and plastic-like materials. It is not necessary (but not precluded, either), that either or both of sheets 242, 244 be a styrene-based or butadiene-based material.

In an exemplary device 240 that is structured as a combination urinal air freshener and drain cleaner, a first fluid 250 (which is a fragrant fluid) is inserted into void 246 by way of first and second puncture holes generally indicated at 252. One puncture hole may admit fluid 250 into the void or cavity 246, while the second puncture hole may release any entrapped air from cavity 246. A seal element, such as a peel-off removable foil cap 184, can then be installed to entrap the fluid 250 during, for example, transportation and handling prior to deployment of that device 240. Similarly, a drain cleaning fluid 254 can be placed into cavity 248. One operable drain cleaning fluid includes tetra sodium ethaline diamine tetracetic acid tetra sodium salt ($C_{10}H_{12}Tv_2O_8Na_4$) or tetra sodium EDTA. Desirably, the puncture holes 252 are sized to operate as discharge orifices permitting a gravity-induced discharge of respective fluid over a desired extended period of time. If required, one or more vent hole may be formed in a sheet opposite to the discharge aperture. Certain embodiments may be self-pressurized to urge fluid flow from a cavity.

Figure 17:
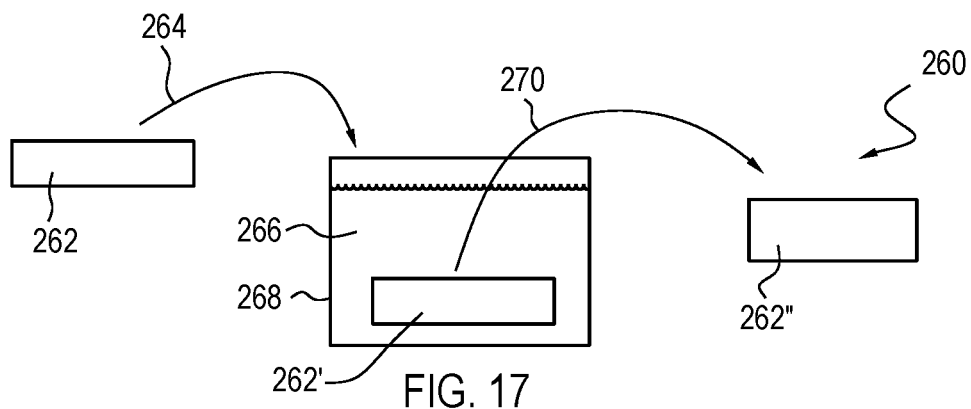
FIG. 17 is a cartoon illustrating operable steps of manufacture of an air freshening material according to certain principles of the invention.

FIG. 17 illustrates one process, generally 260, operable to create an emanator according to certain principles of the invention. One or more piece of carrier material 262 is placed into contact (indicated at arrow 264) with a fragrant fluid, such as fragrant oil 266. Workable carrier materials include styrene-based polymers, butadiene-based polymers, and high-surface area adsorbent materials. As illustrated, the contact can be simple submersion in a container 268, where the material 262' absorbs the fragrant fluid. Desirably, the fluid is maintained at a temperature of between about 20° C. and about 50° C. for a period of time greater than about 2 hours, preferably about 24 hours. The material may then be removed from the fluid, as indicated at arrow 270, resulting in emanator 262". Emanator 262" may be used in an exemplary embodiment 240, such as illustrated in FIG. 15.

Figure 18:
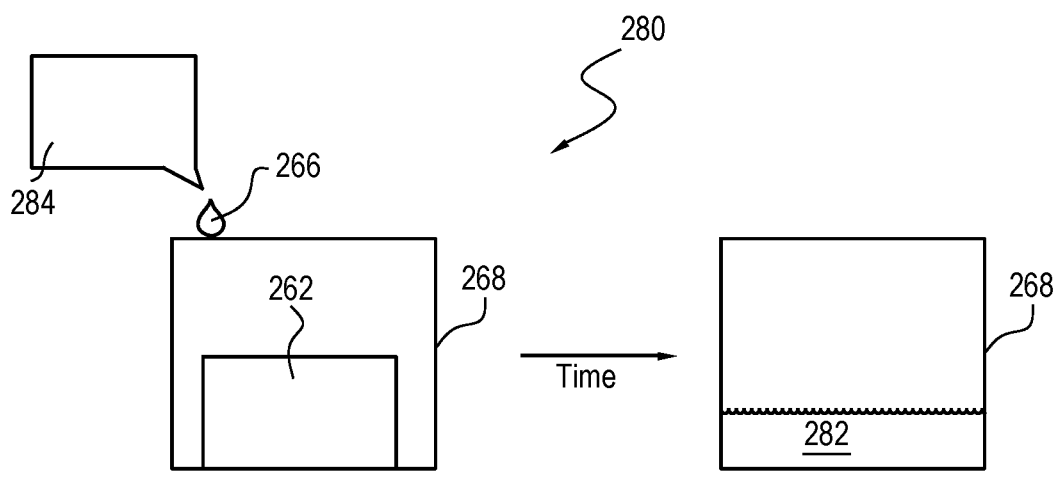
FIG. 18 is a cartoon illustrating operable steps of manufacture of another air freshening material according to certain principles of the invention.

FIG. 18 illustrates a second process, generally 280, operable to form an alternative emanator material 282. A sufficient quantity of fragrant oil is poured from a container 284 onto one or more piece of styrene-based material 262 in a second container 268. After a period of time, and in an ambient fluid temperature between about 25° C. and about 50° C. for a period of time greater than about four hours, the material 262 absorbs a sufficient amount of oil as to change viscosity from a solid to a thick and viscous material. The resulting material 282 may be characterized as a scent-emitting glue-like substance, and is very sticky. The glue-like material 282 may then conveniently be applied as a coating to a substrate, such as screen 102 illustrated in FIG. 1, to form an air fresher. Viscosity of the glue-like material is a function of the amount of fragrance absorbed by the base rubber, or rubber-like, material.

It has been determined by experimentation that only certain rubber, or rubber-like, compositions absorb and release fragrant oil under substantially ambient conditions (e.g. between about 25° C. and about 50° C.). Effective and operable rubber compounds include styrene-based EPDM, natural rubbers, gum rubbers, and cellulosic rubbers.

Figure 19:
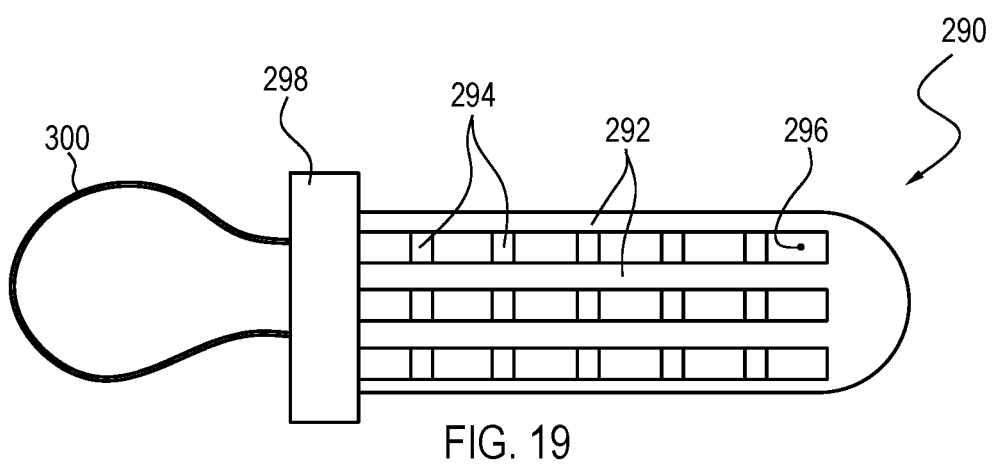
FIG. 19 is a side view of a container in which air freshening material structured according to certain principles of the invention may be placed.

A workable emanator-holding device is illustrated generally at 290 in FIG. 19. Device 290 may be characterized as a thimble, having an internal volume defined by axially extending ribs 292 and circumferentially circumscribing bands 294. Together, the ribs 292 and bands 294 form a plurality of apertures 296. A quantity of emanator material, such as 262" or 282, is placed into the internal volume of container 290, and a cap 298 may be installed to confine the material in place. Desirably, the apertures 296 are sized sufficiently small as to resist escape of a fluid-like material 282. Provision, such as a loop 300, may be included to facilitate suspending device 290 in use as an air freshener. A device 290 may be embodied for direct contact with clothes in a clothes drier, thereby imparting a fresh scent to drying clothes.

Example 1

A piece of styrene-butadiene rubber (SBR) weighing 6.198 grams was dipped into a sufficient quantity of citrus fragrance oil as to be fully submerged. After 12 hours at about 30° C., the SBR piece was removed, dried by paper towels, and weighed. The resulting weight was 14.688 grams. Therefore, the total weight gain was 8.49 grams. That constitutes a weight gain of over 100% at about 30° C. Then, the piece of SBR was placed into a bathroom having an approximately 120 ft$^2$ floor, and the citrus smell filled the room and was initially strong. The citrus smell persisted for more than 30 days.

Various different types of SBR were tested to evaluate the absorption capacity of the rubber. (It should be noted that SBS is also workable). The samples tested had different sources and different thicknesses. Pierced and unpierced samples were also tested. Seven different fragrances were used for absorption tests. The soak times varied from 3 to 6 days for various tests. However, it was established that 3 days was the adequate time period to achieve close to maximum absorption. All tests were conducted at room temperature (72° F.) and weights were measured before and after the soak. The first test was conducted on urinal screen samples similar to those as shown in FIG. 1 and two 1"×1" additional samples. The SBR used was 1/16" thick, red in color and 70-75 A durometer. The results showed that different fragrances differed in their absorption limits.

A test was conducted to evaluate the effect of thickness and piercing on the SBR fragrance absorption. One set of samples was prepared for each of the seven fragrances. Each set consisted of four 1"×1" samples, two each of the two thicknesses, 1/16" and 1/32". Also, one sample from each thickness set was pierced with a Philips head screwdriver to create divots. These were soaked in the fragrances and the results showed that the thinner samples absorbed more weight % of fragrance than the thicker samples. Also, the piercing made very little difference in the absorption capability (2% more weight gain).

Another test was conducted using SBR from two alternative sources. Three samples were prepared per fragrance. Each set of three samples comprised one sample from alternative source 1 and two samples from alternative source 2. The two samples from alternative source 2 had different durometers (75 A and 90 A) while the sample from alternative source 1 had a 75 A durometer. The samples were slightly more than 1/16" thick. The source made a huge difference on the absorption capacity of the SBR. The amount of styrene or butadiene may be responsible for the difference in the absorption capability.

Thinner SBR (1/32" thick) from alternative source 2 was then tested to observe its capability. The absorption capacity increased in most cases. Based on the above tests it can be concluded that SBR has the capability to absorb 5 to 60% of its weight of fragrance.

Example 2

Another sheet of SBR rubber sheet was pierced by a sharp knife at several places to promote an increase in surface area. The perforated rubber sheet was then dipped into fragrance. After about 24 hours in an approximately 35° C. environment, the sheet absorbed more than 75% of its weight in fragrance.

It has been observed that the styrene portion of styrene-based materials can absorb fragrant oil and form a glue-like substance when exposed to liquid scented oil at a temperature between about 25° C. and about 50° C. A trigger event that appears to cause the phase transition between a solid polymer and a glue-like material is addition to the polymer of about 50% (by weight) of fragrance. Preferably, about 75% to 150% of the weight of the styrene-based material will be absorbed during the process to transform a solid polymer into a glue-like fragrant material.

It has also been observed that EPDM and Natural Gum rubbers may also absorb more than about 50% of their weight in fragrant oil, simply by submersion in fragrant oil at substantially ambient temperature for a sufficient length of time. Furthermore, cellulosic rubbers have been observed to operate in a similar manner.

Example 3

In one experiment, 1 g of polystyrene foam obtained from a crushed-up foam coffee cup was placed in a polypropylene cup. 1 g of fragrance was added to the polypropylene cup to bathe the crushed-up foam polystyrene. The fragrance was totally absorbed for a 100% weight gain. Although stirring was not part of the procedure, a viscosity change was detected at an estimated 75% weight gain. After about 4 hours, a fragrant glue was formed from the combination. The fragrant glue was very sticky, and would stick to any surface, especially porous surfaces like paper, cloth, etc. Furthermore, the fragrant glue appears to emit fragrance at a controlled rate. The fragrant glue-like substance was viscous, and would slowly extend in a drip-like extension from a stirring stick used to pick up the mixture. The thusly-formed fragrant glue was placed in a central container of an air freshener device, such as container 130 in FIGS. 3 and 4; the air freshener device was placed in the sink of the aforementioned bathroom; and fragrance level in the bathroom was monitored. The fragrance level was humanly appreciable and relatively constant for a period of time in excess of 18 days.

It has been observed that after losing 20-30% of the fragrance, the "stickiness" decreased. The resulting material then possessed a tacky property similar to a "post-it" note, or glue used to affix a removable object to a substrate. The object can then be removed without retaining residual adhesive, or the adhesive may be easily removed.

Figure 20:
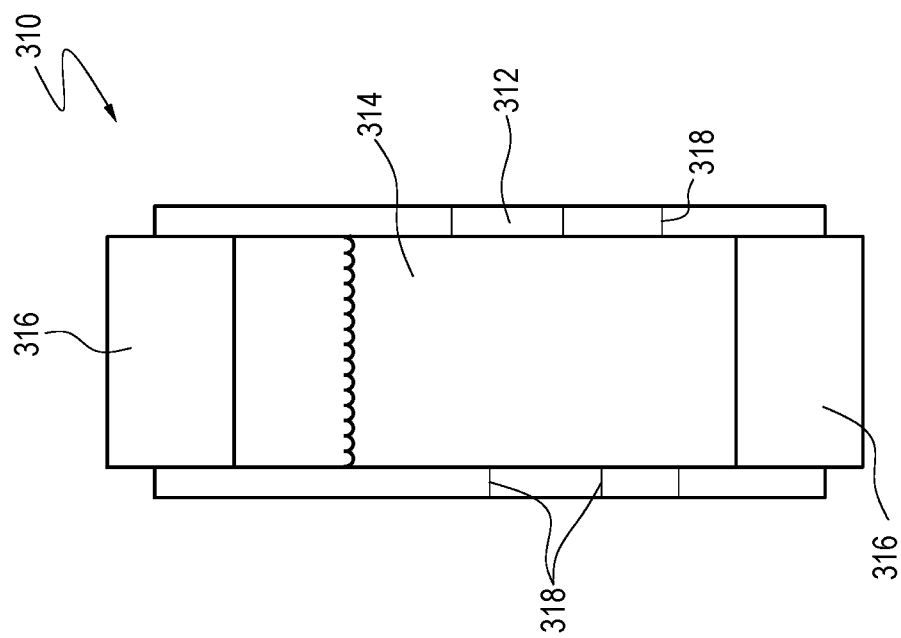
FIG. 20 is a cross-section view in elevation of another embodiment.

The embodiment generally indicated at 310 in FIG. 20 includes an EPDM rubber tube 312, in which may be confined a fragrance or other fluid 314. Tube 312 is capped on its open ends by polypropylene stoppers 316 to resist undesired loss of fluid 314. A plurality of through-thickness punctures or piercings 318 can be created by piercing the tube 312 with a sharp knife. Punctures 318 inherently form very small apertures through which fragrance or other fluids may slowly diffuse to the outer surface for evaporation there-on, or dripping there-from. That is, rubber, and rubber-like materials tend to self-heal to form very small apertures that can permit a slow migration of fluid, or even substantially or completely resist fluid flow. Punctures 318 may also increase the effective surface area of the tube 312. In this kind of punctured embodiment, virtually any sort of rubber, or rubber-like compound, and even some plastic, or plastic-like materials, may be workable.

Figure 21:
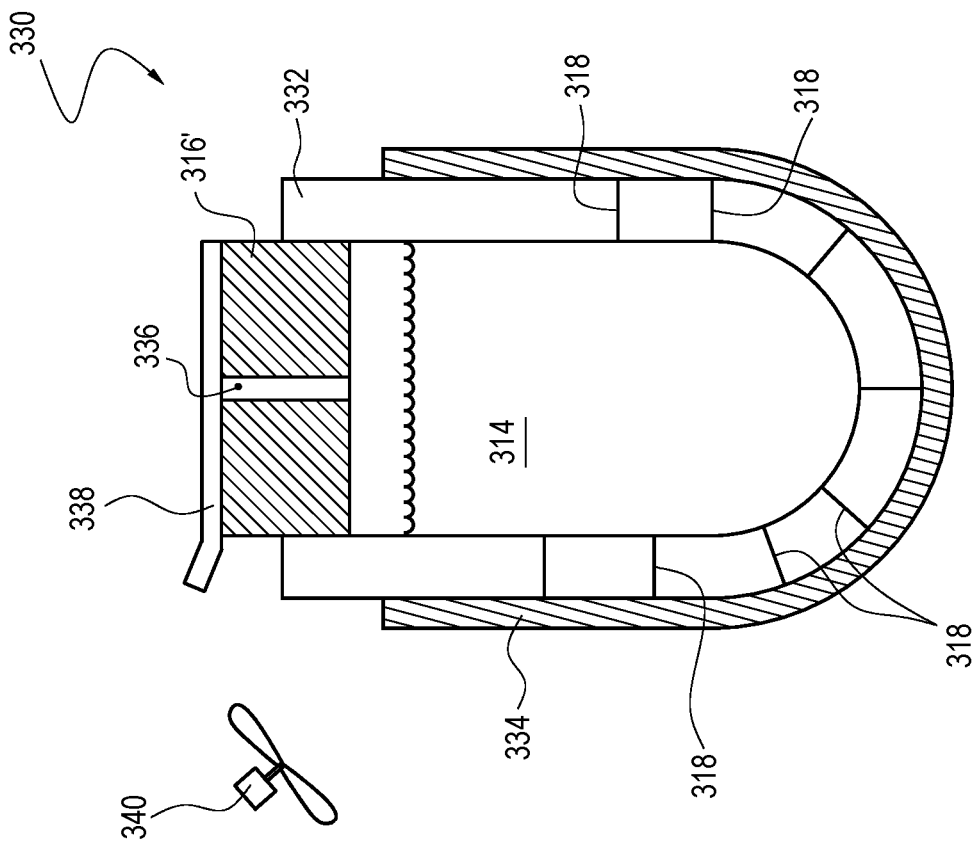
FIG. 21 is a cross-section view in elevation of another embodiment.

For example, the embodiment illustrated in FIG. 21 and generally indicated at 330 includes a container 332 pierced by a plurality of punctures 318. Container 332 may be formed from virtually any rubber, or rubber-like compound, and even some plastic, or plastic-like materials. Bulk fluid 314 migrates through the slits 318 and is dispersed by emanator 334. A workable emanator may be made from paper, or other material that can absorb and disperse fluid for evaporation from an external surface. A stopper 316' includes a fill-aperture 336 that is capped by foil wrapper 338 to resist undesired fluid escape. A fan 340 may sometimes be included to assist in dispersing scent into the environment in which the device 330 is placed into service. In fact, such a fan 340 may be included in any embodiment of the invention, as desired.

Figure 22:
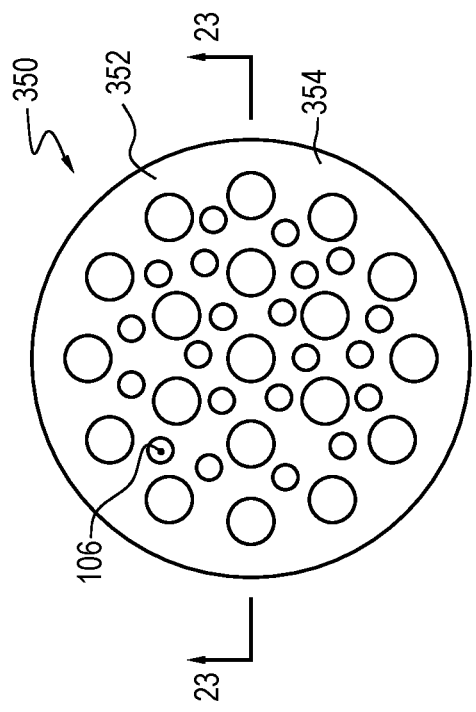
FIG. 22 is a top, or plan view of an embodiment structured similar to bubble wrap, and containing fragrance inside a plurality of bubbles.
Figure 23:
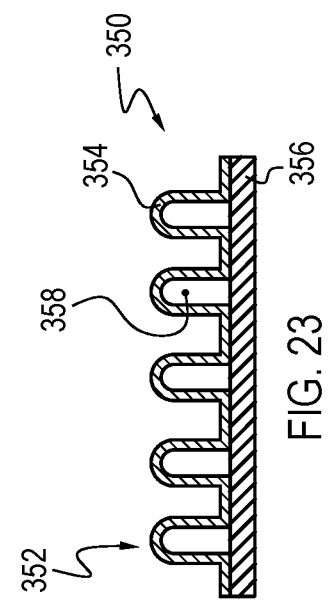
FIG. 23 is a side view of the embodiment in FIG. 22, taken at section 23-23 and looking in the direction of the arrows.

Another embodiment is illustrated in FIGS. 22 and 23, and generally indicated at 350. Embodiment 350 is somewhat analogous to bubble wrap that is used to protect items during shipping. Bubbles, one of which is generally indicated at 352, are formed between top sheet 354 and substrate 356. A beneficial fluid may be loaded into the interior 358 of a plurality of bubbles. Either, or both, of top sheet 354 and substrate 356 may be formed from a rubber or polymer to form an emanator. Beneficial fluids encompass fragrant oils, mosquito repellant, drain cleaners, and the like. The illustrated embodiment 350 is structured to release the bulk fluids at a slow and controlled rate into the local atmosphere or environment in which embodiment 350 is placed into service.

By local atmosphere or environment, it is intended to mean a volume disposed in the vicinity of a deployed device. For example, a local atmosphere may encompass the volume defined by a room in a dwelling or an equivalent space in which a dispensing device is deployed. One such room might encompass a bathroom having a floor sized about 12 feet by 15 feet, or so. Another local environment may be defined by the volume inside a clothes closet. Another local environment may be defined by the volume inside an automobile.

Figure 24:
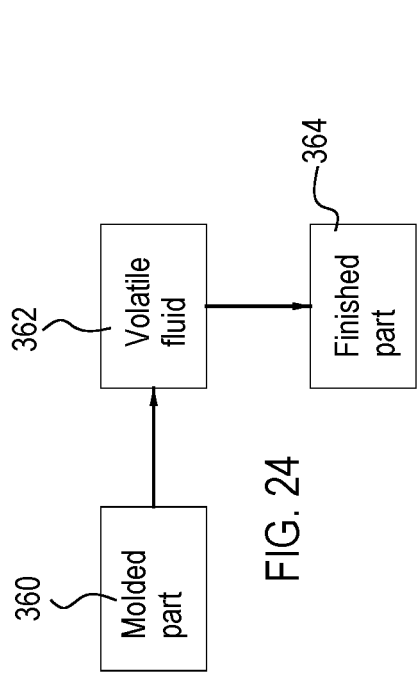
FIG. 24 is a process chart for making one type of embodiment according to certain principles of the invention.

An air freshener according to certain principles of the invention may be very simply manufactured. As illustrated in FIG. 24, an item may be molded or otherwise manufactured in substantially final form from a workable absorbant/releasant carrier material, such as the various rubbers described above, or a material having high surface area per unit weight, or other workable material or combination of materials. The item is desirably provided in substantially final form as indicated in box 360. Then, the item is placed into contact with a quantity of volatile fluid, as indicated in box 362. The fluid is absorbed or infused into the item at substantially ambient conditions (e.g. between about 25° C. and about 50° C.). Time of contact by fluid can be controlled to cause a desired amount of fluid uptake by the item. The result becomes a finished item, ready for service, as indicated in box 364.

Example 4

An embodiment structured according to FIG. 20 was made from a 2 inch length of about 1 inch diameter EPDM tube having a wall thickness of about 1 mm. Several piercings were made in the lower portion of the tube using a sharp knife. A polypropylene stopper was inserted into the bottom, and the tube was half-filled with fragrance. The tube was then sealed with a top polypropylene stopper, and the assembly was placed into an open container. The container was placed into a small bathroom, where the fragrance emanation has remained humanly detectable at a strong level for over 28 days.

Example 5

An embodiment similar to FIG. 1 as mentioned in EXAMPLE 1 was tested for fragrance delivery in a urinal environment. The Urinal Cover samples consisted of one sheet of 1/16" thick red SBR with 70-75 A durometer. They were soaked in six different fragrances and were then tested for fragrance delivery. Two samples were tested per fragrance. One sample was placed submerged in a water trough while one sample was kept unsubmerged. The sample in the trough was to simulate urinals which retain water while the unsubmerged sample was meant to simulate urinals that do not retain any water after flushing. Urea was added to the trough containing the submerged sample and it was left for an hour. This water was drained over the unsubmerged sample to simulate the flushing action for both the samples. Water with urea was then added to the submerged sample and then the process was repeated every hour for nine hours to simulate an office environment use. Samples from all six fragrances were tested this way.

The tests showed that the samples delivered fragrance for more than 20 days. They also delivered between 85 to 95% of the absorbed fragrance indicating a minimum waste in fragrance used. The fragrance delivery rates were comparable if not higher than those obtained from existing market products. Also, the amount of fragrance delivered was a lot higher than the existing market products. The fragrance level was humanly perceptible even towards the end of the testing period.

The terms "fragrance" and "fragrant oil", and the like are sometimes employed as a convenience in this disclosure to characterize bulk volatile fluids. These terms are intended to encompass any volatile or beneficial fluid or agent, irrespective of any scent characteristic of the fluid. Beneficial agents include volatile and non-volatile fluids that are beneficial for the environment surrounding the emanation of such fluids. Exemplary beneficial agents nonexclusively include mosquito repellant, citric oils, cleaners, deodorizers, moisturizing liquids, air care products, medicinal fluids, and the like.

Exemplary materials for use as an absorber/releaser or emanator in certain embodiment of the invention include styrene-based polymers such as: acrylonitrile-butadiene-styrene (ABS), styrene-butadiene-styrene (SBS), styrene-acrylonitrile (SAN), styrene-isoprene-styrene (SIS), styrene-ethylene-butadiene-styrene (SEBS), styrene-ethylene-propylene-styrene (SEPS), and combinations thereof; and operable styrene-based rubbers non-exclusively include: styrene-butadiene-rubber. As previously mentioned, EPDM, Natural rubbers, and cellulosic rubbers are also operable, among other workable compositions. An emanator may be fashioned from butadiene-based polymer materials, and combinations of styrene-butadiene-based materials. Furthermore, heat-shrinkable polymeric material and nano-porous polymeric material are also workable to form containers in which to confine bulk volatile fluid. In certain preferred embodiments, a portion of the walls of a container inherently form an operable emanator.

Also, as previously indicated, certain embodiments are operable even if the base material used to confine a bulk fluid does not significantly absorb and subsequently release the bulk fluid (i.e. a fragrance, volatile oil, or other beneficial fluid) at approximately ambient temperatures on the planet Earth. For example, no significant fragrant oil uptake was observed for Silicone rubber, polypropylene, polyethylene, acrylic rubbers, PVC, EVA at approximately room temperature (about 20° C.). However, embodiments structured according to certain principles of the invention may encompass a bulk fluid container made from, or including, one or more of such materials.

Figure 25:
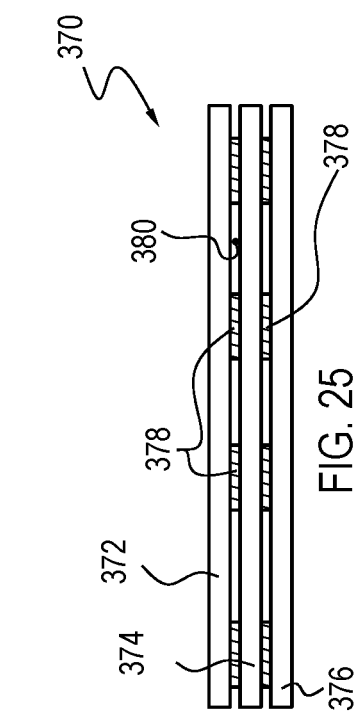
FIG. 25 is a side view in perspective of a portion of an air freshener including micro-channel structure according to certain principles of the invention.

A workable embodiment may include an emanator that can be structured to include microporous or nanoporous elements. Further, a workable emanator can include microchannels. A workable emanator can be thought of as a sponge, and structured accordingly. For example, FIG. 25 illustrates a portion of a microchannel emanator. The illustrated emanator, generally indicated at 370, is formed by a series of stacked and bonded-together sheets and spacers. Any number of sheets and spacers may be employed, as desired. A small sample is illustrated for convenience. Top sheet 272, middle sheet 274, and bottom sheet 276 form top and bottom surfaces for contact with fragrance fluids. A plurality of spacers 378 form sides, or walls, of a plurality of microchannels 380, in which to receive a fragrant fluid. The fragrance can be injected into, or aspired subsequent to evacuation of air from, the channels 380.

Preferably, the sheets 272, 274, and 276 are formed from a material that absorbs and subsequently emanates fragrance. However, certain alternative embodiments may rely only upon evaporation or emanation of scent from the open ends of the microchannels 380. Microchannels can be sized in any workable range operable to maintain capillary attraction to the fragrant fluid employed in a device. For non-limiting example, channel height can be between 10 and 100 µm; channel width can be 10 to 500 µm; and sheets can be 50 to 200 µm thick, or so.

Figure 26:
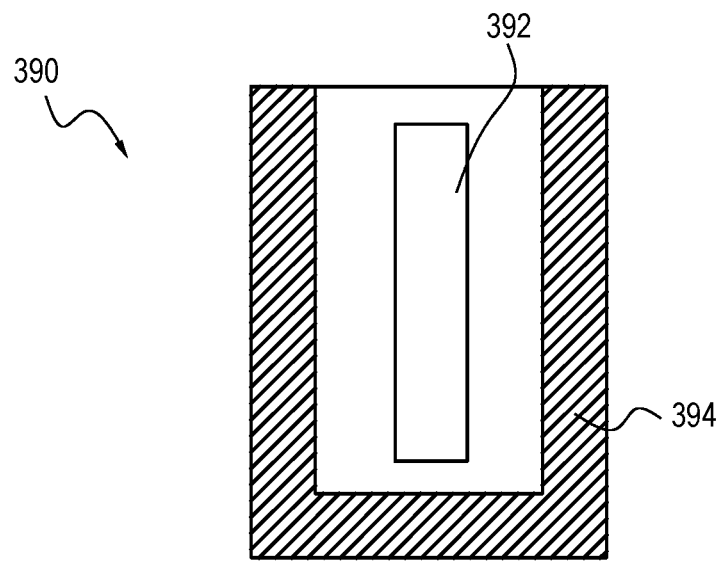
FIG. 26 is a side view, in cross-section, of another embodiment structured according to certain principles of the invention.

It is within contemplation that certain embodiments may include a heating element to facilitate, or accelerate, emanation of fragrance. For example, FIG. 26 illustrates a heated embodiment, generally indicated at 390, which includes an emanator 392 that is warmed by a heating element 394. An operable heating element 394 may be battery operated, or obtain electrical energy by a conventional cord-and-outlet arrangement. A workable dispensing device may be structured to include a combination of elements that are individually extracted from any of the various embodiments described in this disclosure.

Figure 27:
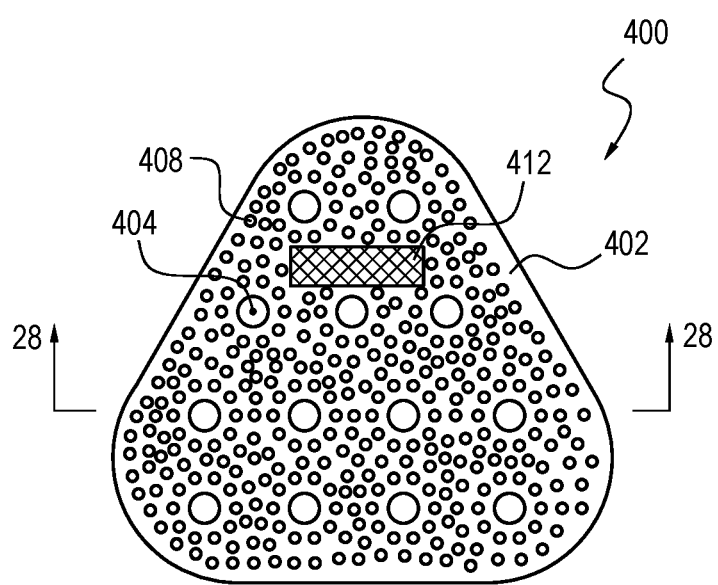
FIG. 27 is a plan view of an air freshener structured for use as a urinal screen.

FIG. 27 illustrates a dispensing device, generally 400, particularly adapted for use in a urinal air freshening application. A support 402 is pierced by drain holes 404 and carries splash-resisting bristles 408, and a life-indicator, such as dye-indicator strip 412. Desirably, a life-indicating element such as 412 is visible during the time the device 400 is in service, and provides a visual indication of the remaining operable life of the device 400.

Figure 28:
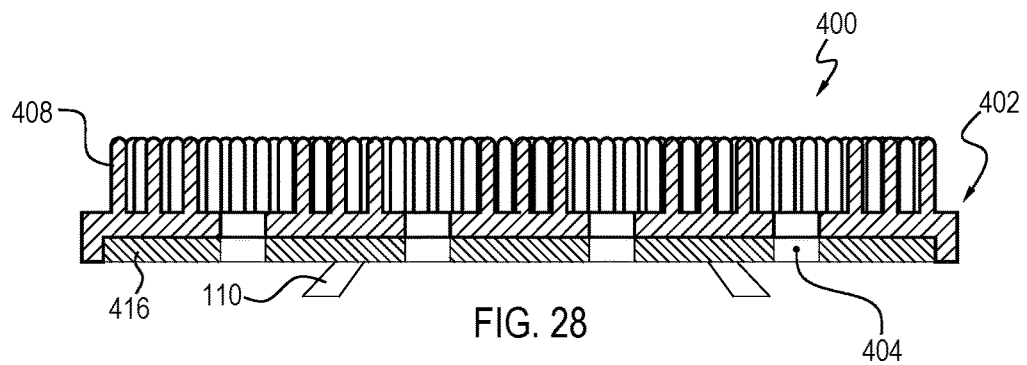
FIG. 28 is a cross-section view taken at section 28-28 in FIG. 27.

As shown in FIG. 28, illustrated support 402 is a cover that carries a plurality of bristles 408 configured to disperse a stream of fluid as an operable splash-guard to resist splash of that fluid. Reduction in splash of urine provides an improved health and cleanliness benefit. Cover 402 also forms a housing in which to dispose an air freshening element, such as emanator 416. Desirably, a cover 402 may be formed from a low-cost polymer, plastic or plastic-like material, such as polyethylene, polypropylene, polyester, recycled polymer material, PVC, and the like. An emanator 416 may be formed from a more expensive material or combination of materials, and then added to the support or cover 402. An operable emanator 416 may be formed by a suitably shaped piece of carrier material (such as SBR) that is pre-loaded or infused with a fragrant volatile fluid, and may be configured as a replaceable insert, cartridge, or element. Legs 110, or other support structures, may be provided to operably interface with cooperating structure present at a particular deployment location.

Figure 29:
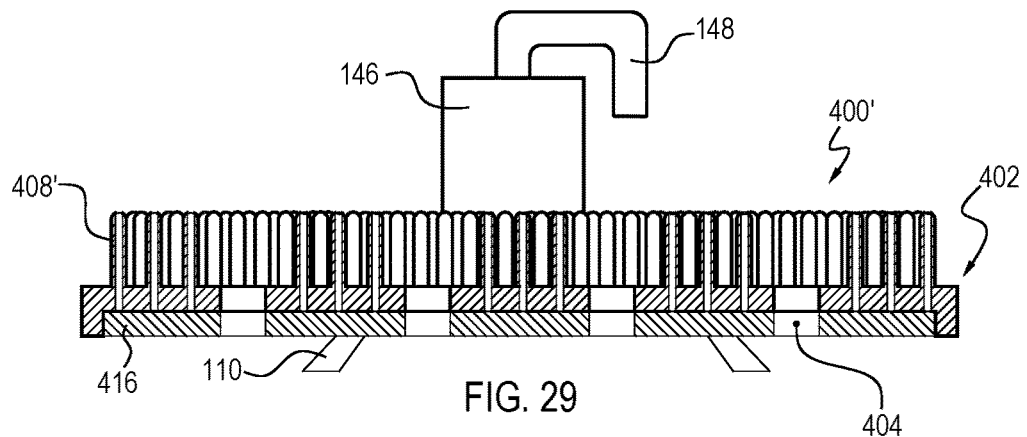
FIG. 29 is a view similar to that in FIG. 28, but illustrating an alternative embodiment.

A similar embodiment 400' illustrated in FIG. 29 further includes a dedicated dispenser 146 for a drain cleaning solution. Bristles 408 are configured to disrupt and resist splash of a fluid stream. Alternative hollow bristles 408' that serve the same splash-resistance or knock-down function may be provided to enhance release of fragrance from an emanator 416 that is disposed underneath a cover or support 402. Again, a splash guard 148 may be provided to resist fluid entrance into a vent of the drain cleaner assembly 146.

Figure 30:
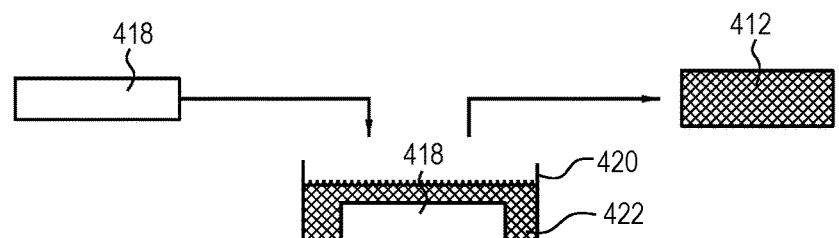
FIG. 30 is a depiction of a manufacturing process for an exemplary embodiment.
Figure 31:
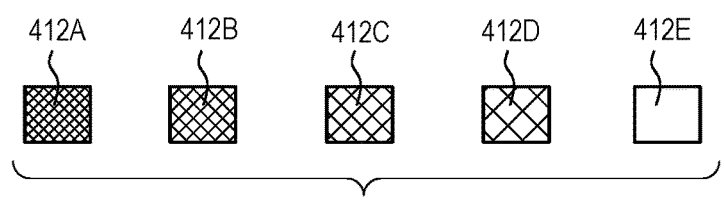
FIG. 31 illustrates an embodiment subsequent to passage of time.

FIG. 30 illustrates manufacture of a workable life-indicating strip 412. A workable carrier substrate, such as a length of styrene-based polymer material 418, is placed into a container 420 and submerged in a fluid dye 422. Fluid 422 may also include a fragrant volatile fluid, and thereby form a dual-purpose life-indicating and fragrance-dispensing element 412. An indicator structure may be formed by combining a dye with a volatile fluid (e.g., fragrant oil, acetone, etc.), and applying that fluid to a carrier substrate. An indicating glue may even be formed after the substrate absorbs a sufficient quantity of the volatile fluid. As shown in FIG. 31, an indicator strip 412A is initially fully dark or colored prior to deployment of a dispensing device, such as dispensing device 400 in FIG. 27. The color or intensity of color of indicator 412 gradually decreases as indicated by 412B, 412C, 412D, and 412E. Desirably, the change in intensity or color is approximately linear and relatively constant during the life of the dispensing device, so by the time the indicator 412 is in expired condition as indicated at 412E, the fragrance-dispensing capability of the representative device 400 is also nearly or completely expired.

FIGS. 32 and 33 illustrate another variation of a dispensing device, generally indicated at 440, adapted as a urinal air freshener within the ambit of the invention. Dispensing device 440 includes a cover 402 that advantageously may be made from various low-cost polymer materials, such as polyethylene, and the like. A holder, generally 444, receives a fragrant element 448, and a drain cleaning fluid dispenser 452. The holder 444 and/or one or more foot element 110 may be structured to interface with 3-dimensional structure in an area in which the device 440 is deployed. A preferred fragrant element 448 includes a fragrance-infused polymer material, such as SBR. A workable drain cleaning fluid dispenser 452 may release fluid under influence of gravity, or in accordance with any of the previously-described embodiments of fragrance or volatile or cleaning fluids, or combinations thereof. Either or both of elements 448 and 452 may be made as replaceable cartridges structured for cooperating reception in holder 444.

FIGS. 34 through 36 illustrate details of a size-adjustable embodiment, generally indicated at 460. Sometimes, it is desirable to change the amount of an active agent a dispensing device will broadcast into an environment. Other times, it may be desirable to change a deployable size of a working surface area to fit into a particular space. As illustrated, embodiment 460 can be configured to change its deployed working area to fit into a urinal of a particular size. Embodiment 460 includes column and row spacer elements that are structured to be additive or subtractive. One or more column 464 of spacer elements may be removed or added to change the width of the device 460. Similarly, one or more row 468 of spacer elements may be removed or added to change a length of the device 460. A backing element 472 may be provided to reinforce an assembly against undesired separation of spacer elements. If a row 468 or column 464 is removed, the sides remaining behind are structured to connect together. In the illustrated embodiment 460, the elements fit together like puzzle pieces. However, alternative connection structures (e.g. snaps, hook-and-loop, interlocking tongue-and-grove, etc.) are also operable. More complex spacer shapes are contemplated to permit alternative changes in shape of a working surface area.

Figure 38:
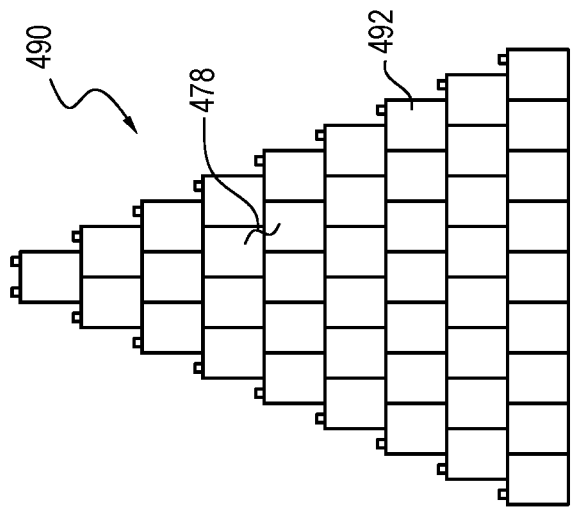
FIG. 38 is an alternative size-adjustable fragrance delivery device.
Figure 37:
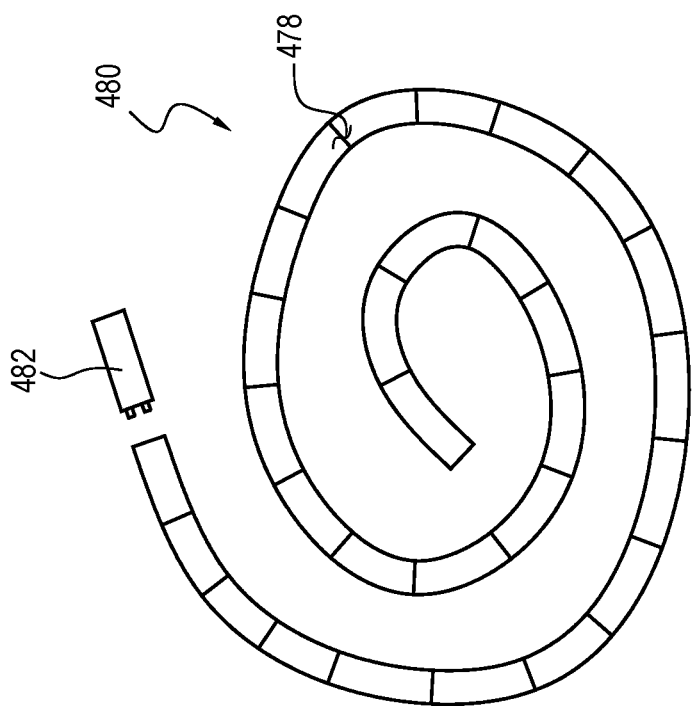
FIG. 37 is an alternative size-adjustable fragrance delivery device.

FIGS. 37 and 38 illustrate two embodiments that each have size-variable deployment areas 478. The snake-like embodiment, generally 480, in FIG. 37 includes a plurality of constituent elements 482 disposed in an end-to-end, or front-to-back coupling assembly. A front surface of each coupling element 482 carries male coupling structure 484, and a back end of each element 480 carries cooperating female coupling structure. An elongate or snake-like body of any desired length may be assembled from the requisite number of elements 482. In the illustrated embodiment 480, the coupling structures and bodies may be structured from or comprise materials operable to provide sufficient flexibility as to permit bending the assembly into a spiral or other nonlinear shape.

Figure 39:
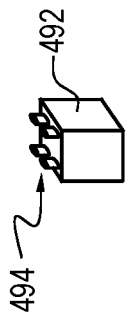
FIG. 39 is a view in perspective of a constituent element of the embodiment in FIG. 38.

The monolithic embodiment, generally 490, in FIG. 38 similarly has constituent elements 492 having cooperating male and female connection structures disposed at opposite ends. FIG. 39 illustrates one example, generally indicated at 494, of workable male coupling structure. Individual coupling elements 482, 492 may be made from a carrier material that is infused with a desired quantity of a volatile fluid, such as a fragrant oil.

A deployed area 478 inherently contains a number of constituent coupling elements. Each constituent element makes a contribution by providing a surface area from which volatile fluid may evaporate to dispense an agent into the local atmosphere. A larger deployed area 478 exhibits a more apparent and detectable distribution of active or operable agent to a local environment compared to a smaller deployed area. When a device, such as 480 or 490, is an air freshener, the assembled area 478 forms an emanator. The larger the deployed emanator area, the more scent that will be deployed to the local environment. Therefore, an air freshener, such as distribution device 480 or 490, may be assembled and sized to operate to a desired extent (e.g., broadcast a scent at a desired detection level) in a plurality of environments having different sizes.

Sometimes, it is desirable to prove structure arranged to enhance release of volatile fluid molecules from an emanator, or to maintain emanation of a volatile agent at or near an initial pace. A few non-limiting examples are illustrated in FIGS. 40-45. Certain embodiments may include fluid distribution structure configured to maintain an enhanced wetted emanator surface area size as the volatile fluid is depleted. An enhanced wetted surface area is larger than the area that would conventionally be wetted as the fluid is depleted. For example, the wetted area of a cylindrical container of fluid is conventionally reduced in concert with reduction in height or depth of fluid as the fluid is dispensed to the local environment. That is, part of the potential emanator area may effectively become dry in certain embodiments that lack the enhanced wetted area functionality.

Figure 40:
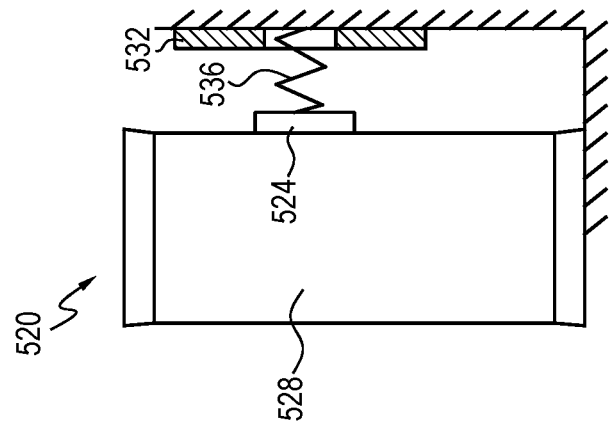
FIG. 40 is a plan view of an alternative embodiment.

The embodiment indicated at 520 in FIG. 40 shows a vibrating element, such as magnetically attracted disk 524, arranged to impart mechanical energy to an emanator surface of pouch 528. A workable pouch 528 may be formed from tubular heat-shrinkable polymer or nano-porous material. An exemplary heat shrinkable material exhibits a 2:1 shrink ratio. Ends of such a tube may be heat sealed to form a container or pouch 528 in which to hold a quantity of volatile fluid, or a source of volatile fluid, and walls of the pouch can also operate as an emanator. One side of the disk 524 is affixed to a surface or wall of pouch 528. The other side of disk 524 is normally biased away from the intermittent magnet 532 by way of spring 536. Oscillation of the magnetic field from magnet 532 causes the disk 524 to shake a wall of pouch 528, and thereby, increases diffusion and causes an enhanced emanation of volatile fluid from pouch 528.

Figure 41:
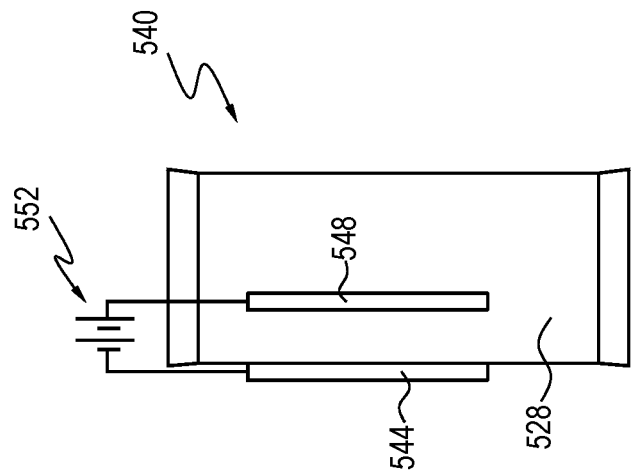
FIG. 41 is a plan view of an alternative embodiment.

The embodiment generally indicated at 540 in FIG. 41 shows application of an electric potential across a wall of a pouch 528. Electrode 544 is disposed external to the pouch 528. Electrode 548 is disposed inside the pouch 528 and is wetted by volatile fluid. A voltage source, generally 552, is connected to the electrodes 544 and 548. Application of a potential across the pouch wall may assist in, or enhance, emanation of volatile fluid molecules from the pouch 528.

Figure 42:
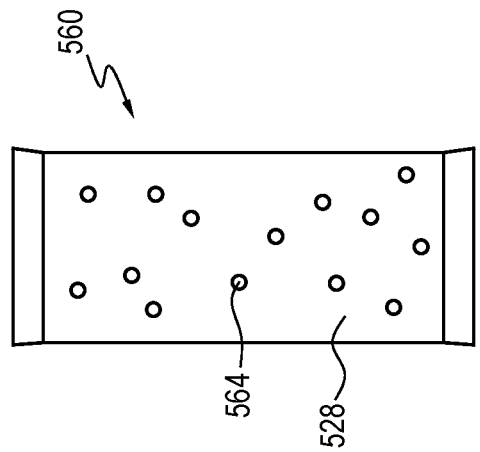
FIG. 42 is a plan view of an alternative embodiment.

The embodiment generally indicated at 560 in FIG. 42 shows a pouch 528 carrying an internally disposed gas-generating compound, along with a volatile fluid. Moisture present in the local environment may diffuse through the wall of pouch 528 and interact with the gas-generating compound 564. The generated gas can increase internal pressure inside pouch 528, and thereby, enhance emanation of volatile fluid molecules from the pouch 528. An operable gas-generating compound includes citric acid and sodium bicarbonate. Moisture may alternatively be applied in other ways, as desired.

The embodiment generally indicated at 570 in FIG. 43 shows a pouch 528 carrying an internally disposed wicking element 572. A workable wicking element 572 can be saturated by volatile fluid, or be disposed in an excess quantity of volatile fluid, and is operable to distribute that fluid to wet the inner surface of a pouch 528 or other container. In that way, the wetted emanator surface can remain essentially the same size as the original deployed wetted surface during the entire time that the volatile fluid is evaporating from an exterior emanator surface. The operable exterior emanator evaporation surface can remain at the corresponding same deployed size. Therefore, when the volatile fluid produces a scent, the scent can remain substantially constant to human perception over a longer period of the operable life of a broadcast or distribution device in which a constant emanator-area device, such as embodiment 570, is deployed. An exemplary wicking element 572 is a sponge.

A mechanical device may sometimes be employed to maintain an enhanced size of an emanator surface in a wetted condition. For example, the air freshener device generally indicated at 576 in FIGS. 44 and 45 is structured to rotate a container 578 of volatile fluid operably to apply volatile fluid to a larger area of emanator than would be the case if the container 578 were stationary. Embodiment 576 includes a housing or body 582 in which are held the control system 582, motor 584, and power supply 586. A workable power supply 586 may include a rechargeable battery, or super capacitor. Alternatively, a cord may be provided for plugging in to an electric outlet. Certain embodiments may include a charging device in-circuit with the power supply, such as solar cell array 588.

Body 580 includes a plurality of openings 590, through which air may circulate to dispense an agent into the local environment. The agent typically includes molecules of a scented volatile fluid 592, which evaporate from the evaporation surface 594 of the emanator 596. Volatile fluid 592 diffuses through the emanator 596 from a wetted side to the evaporation surface 594. Again an operable membrane/emanator 596 may be formed from a heat-shrinkable polymer material or nano-porous material. It can be seen that as the fluid level 598 drops, rotation of container 578 causes membrane 596 to pass through the pool of fluid 592, thereby maintaining a larger wetted surface area. It is within contemplation to dispose an alternative or supplemental membrane/emanator 596 on the circumferential surface of container 578 as indicated at 600 in FIG. 45. In that case, the circumferential surface 600 will operate as an emanator that is wetted by rotation of the container 578 until the fluid 592 is completely consumed. That is, rotation 602 of the container 578 moves surface 600 through a bath of fluid 592 until the fluid is depleted and the corresponding agent is fully broadcast into the local environment.

Another embodiment according to certain principles of the instant invention includes high-surface area adsorbent materials that are loaded with a volatile fluid. For purpose of this disclosure, a high-surface area material is a material that exhibits greater than about 10 $m^2/g$ of surface area to weight or mass on the surface of the Earth. The fluid-loaded adsorbent materials may be employed directly as a stand-alone emanator, or may be disposed inside a container of some sort. Exemplary adsorbent materials include molecular sieves, zoolites, silica, silica gels, activated carbon, high surface area metal powders such as Iron, Magnesium, and activated Alumina, and the like. A workable container may operate, for example, to maintain a collection of adsorbent material (e.g., in pellet or granular form, or in the form of a quantity of powder), in an organized state and in a desirably small volume. Certain containers simply look nice to a consumer. A currently preferred container is manufactured from a membrane, especially including a membrane formed from heat-shrinkable polymer material or nano-porous polymer material, wet cell battery separator, and the like. When present, the membrane desirably operates as an emanator.

Figure 48:
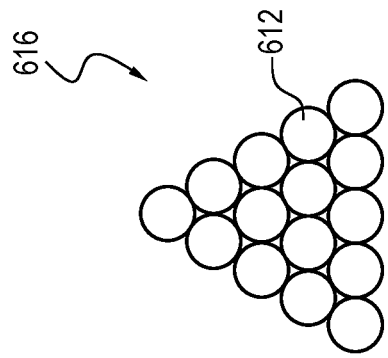
FIG. 48 is a plan view of an alternative embodiment.
Figure 47:
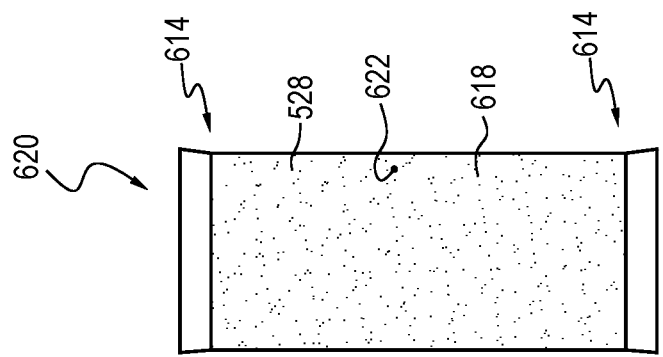
FIG. 47 is a plan view of an alternative embodiment.
Figure 46:
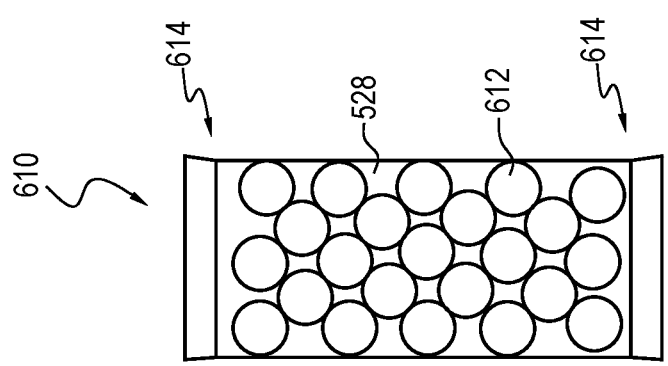
FIG. 46 is a plan view of an alternative embodiment.

Exemplary embodiments with an emanator that includes high-surface area adsorbent materials are illustrated in FIGS. 46 through 48. The embodiment indicated generally at 610 in FIG. 46 includes a plurality of activated Alumina pellets 612 disposed inside a pouch 528. The pellets 612 may be pre-loaded with volatile fluid, or may be bathed in an excess quantity of volatile fluid inside the pouch 528. Preferred embodiments include heat-sealed ends 614. An advantage provided by certain pre-loaded pellets 612 is that, in the event of rupture of the pouch 528, the volatile fluid is confined to the pellets, and will not cause a fluid spill and attendant stain of a surface on which the pellets 612 fall.

Figure 49:
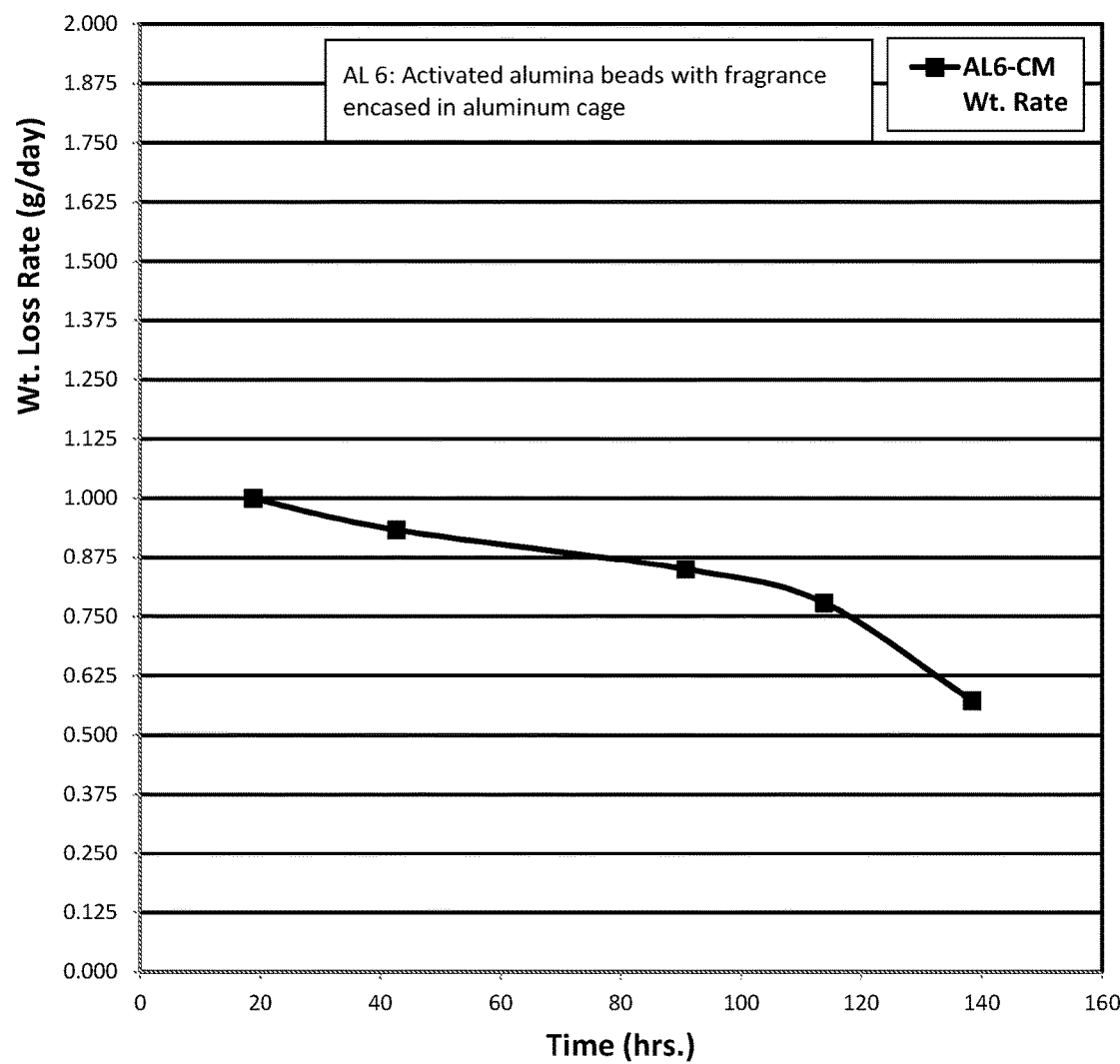
FIG. 49 is an X-Y plot showing release of volatile fluid over time by the embodiment in FIG. 46.

An exemplary embodiment 610 was formed from high-surface activated alumina pellets 612 obtained from the Alfa-Aesar company. Alph Aesar Company has a web site located at world wide web alfa.com. The pellets 612 were placed in a 300 degrees C. environment for a period of 24 hours to drive off any adsorbed moisture, then cooled to room temperature. 15 grams of fragrant volatile fluid was added to 20 grams of Alumina pellets 612 at room temperature. A vacuum was then applied to the mixture to remove any adsorbed air from the pellets. It was observed that all of the volatile fluid was adsorbed by the pellets 612. The loaded pellets were then encased in polyolefin heat-shrinkable tubing exhibiting a 2:1 shrink ratio. Ends of the tube were heat-sealed as indicated generally at 614. The resulting container 528 was exposed to a local atmosphere, and delivery of the volatile fluid molecules to the local environment was measured as a function of time. Results of the measured change in container weight over time are presented in FIG. 49. It is within contemplation that loaded pellets 612 (or other forms of high-surface area materials) may be employed directly as an emanator, as indicated generally at 616 in FIG. 48.

Figure 50:
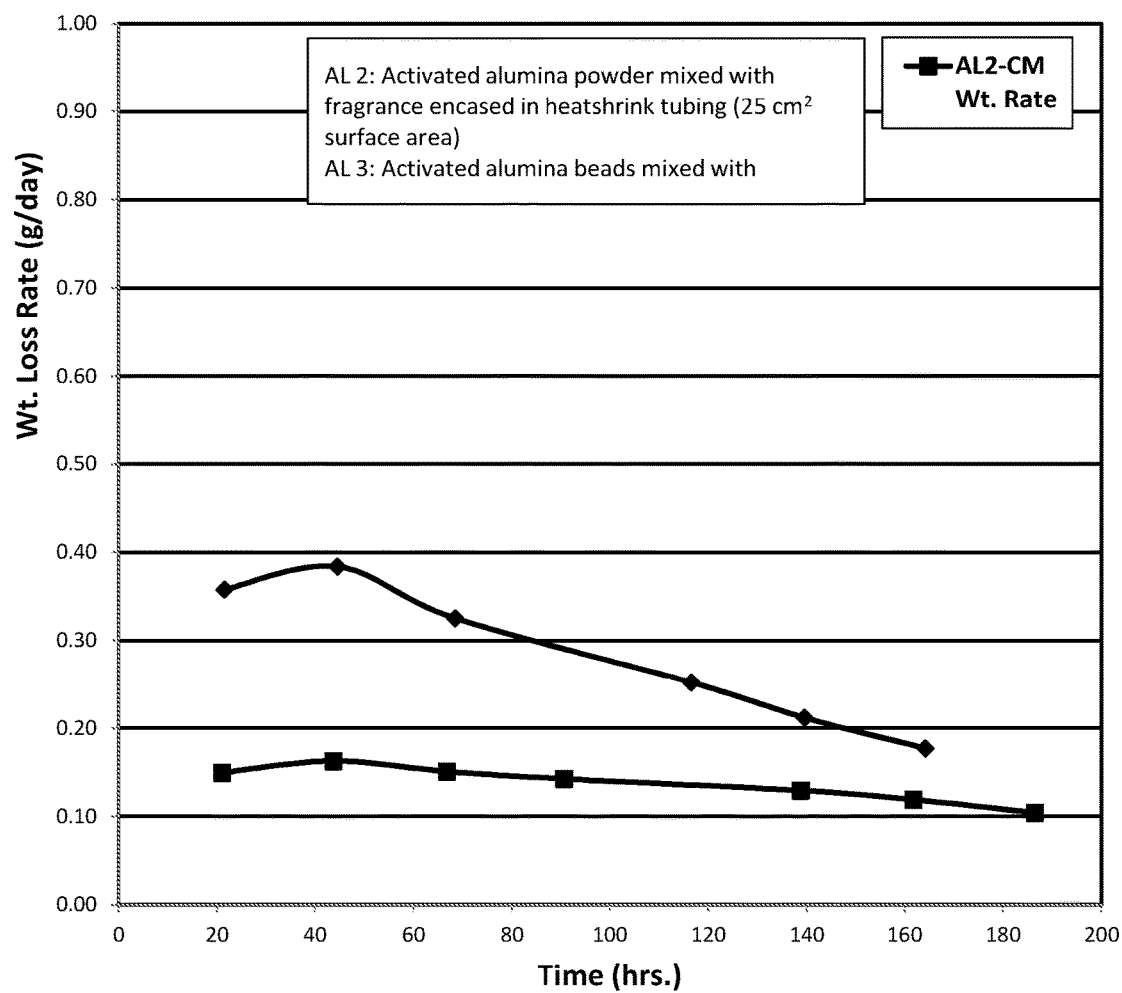
FIG. 50 is an X-Y plot showing release of volatile fluid over time by embodiments such as illustrated in FIG. 47.

Another embodiment is indicated generally at 620 in FIG. 47. Embodiment 620 was made by extracting high-surface area γ Alumina powder straight from a bottle, e.g., without additional processing to remove moisture. The particle size of the powder was between about 150 to about 200 microns. A total of five g of γ Alumina powder was added to 4 cc of fragrance (e.g., a volatile fluid). The Alumina soaked up all of the fragrance. The loaded powder 618 was then disposed in volume 620 inside a polyolefin heat-shrinkable tubing exhibiting a 2:1 shrink ratio. Ends of the tube were heat-sealed as indicated at 614. The resulting container 528 was exposed to a local atmosphere, and delivery of the volatile fluid molecules to the local environment was measured as a function of time. Results of the measured change in container weight over time are presented in FIG. 50.

Figure 51:
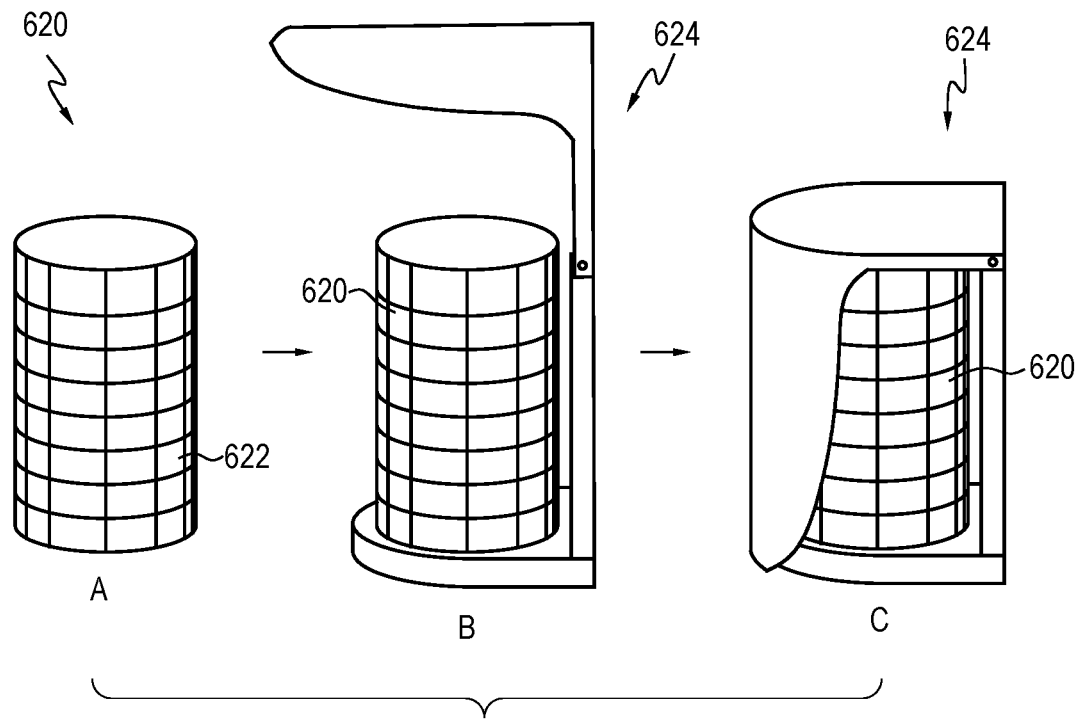
FIG. 51 illustrates an emanating cartridge and a holder.

As illustrated in FIG. 51, an air freshening emanator 620 according to certain principles of the invention may be embodied as a replaceable cartridge 622. Exemplary cartridges 622 are structured for cooperation with an attractive holder 624. A holder 624 and cartridge may be structured to permit naturally occurring air currents to convey the emanations for distribution into the local environment. However, a fan or other element may be provided to assist in delivering a desired quantity of air-freshening agent in a particular volume. When the air freshening capacity of a cartridge 622 is sufficiently diminished, the spent cartridge 622 may be exchanged for a fresh replacement cartridge 622. Certain embodiments may include visual feedback to indicate remaining useful life, as described in detail above. Sometimes, a cartridge 622 may be used in single or serial consumption on its own, without a holder 624. Also, a holder 624 may be structured to contain a plurality of cartridges 622 for use in parallel, and the number of installed cartridges may be increased as desired e.g., to treat a larger volume.

Figure 52:
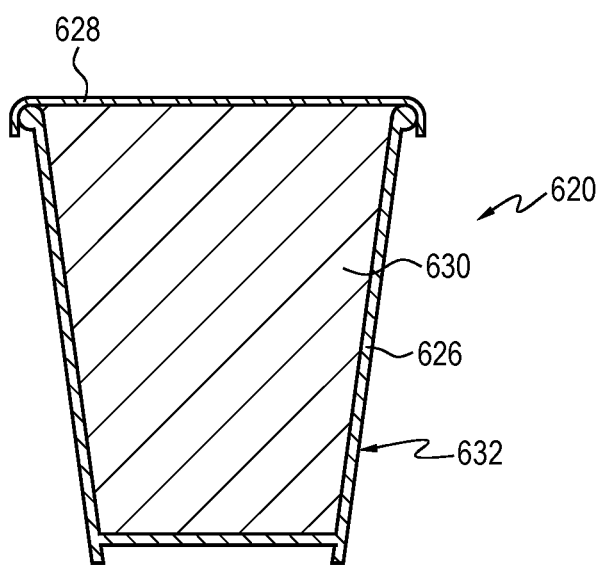
FIG. 52 is a cross-section view in elevation of a workable emanating cartridge.

The exemplary emanator 620 illustrated in FIG. 52 includes a container 626 and a lid 628. Sometimes, the lid 628 may not be included. A quantity of volatile fluid-loaded emanating material 630 (e.g., fragrance-loaded, or fragrant oil-loaded) is held inside the container 626. A workable container 626 may be structured like a conventional paper cup. Desirably, the wall, floor, and/or lid 628 of the cup is made from a material that is absorbent and emanating of volatile fluid, such as certain of the materials described above in connection with other embodiments. In that case, fluid can be transported from inside the container 626 and the wall, floor, and/or lid 628 forms a surface of enhanced size from which the volatile fluid may evaporate to dispense volatile fluid into the environment. It has been determined that plain paper works quite well as an emanating wall 626. Porous cellulose paper, such as a commercially available bathroom paper towel, or blotter paper, can form exemplary embodiments of an emanator. Other emanating materials discussed above are also workable.

In FIG. 52, the wall 632 of container 626 provides sufficient structural support to hold the material 630 in a particular shape. Although material 630 in FIG. 52 is illustrated as a solid mass, alternative particulate and other arrangements are workable. It is within contemplation that alternative containers may require a support of some sort to maintain a shape. The wall 632 also emanates the volatile fluid, so serves a plurality of purposes. Among over functions, a wall 632 may also be infused with a dye agent to indicate remaining useful service life. A wall 632 may also carry attractive visual decorations, as is known in the art.

A volatile fluid-loaded material, such as emanating material 630 in FIG. 52, may include one or more material and be made as variously described above. It is currently preferred for a material 630 to encompass one or more primarily adsorbent material having a surface area greater than about 10 $m^2/g$, 20 $m^2/g$, 30 $m^2/g$, 40 $m^2/g$, 50 $m^2/g$, 60 $m^2/g$, 70 $m^2/g$, 80 $m^2/g$, 90 $m^2/g$, or 100 $m^2/g$. More preferred adsorbent materials have a surface area that is greater than about 200 $m^2/g$. Exemplary such materials include ceramic materials, Alumina, γ-form Alumina, Silica, ceramic, activated carbon, carbon black, molecular sieves, and zeolite. Some operable adsorbent materials may possess a surface area of 300 $m^2/g$, or 350 $m^2/g$, or more.

Fluid uptake for an adsorbent material may be characterized as a surface area phenomenon. It has been observed that certain high-surface area carrier materials have greater affinity to water molecules than to certain volatile fluids. Consequently, volatile fluid is displaced from the carrier material by the application of moisture to, or equivalently, uptake of moisture by, the carrier material.

The various constituent material(s) may be in powder, meal, granular, bead, chunk, briquette, brick, or larger-scale form. Currently preferred adsorbent material is deployed in spherical bead form and having a diameter of ⅛ inches, ¼ inches, ⅜ inches, ½ inches, or more, and sometimes, less. Sometimes, a volatile fluid emanating material 630 may be manufactured to resemble bread or cookie dough, or even glue having a selectable range of viscosity from paste to thin syrup. It is within contemplation that net-shape objects of any desired shape may be manufactured to include one or more such high surface area adsorbent material for use in certain embodiments. For example, a component may be injection-, or otherwise molded to include one of the aforementioned materials, then loaded with a volatile fluid to form an emanating structure having a defined shape. One workable way to load a component with volatile fluid is by soaking the component in the volatile fluid for a period of time, as detailed above.

Sometimes, a volatile fluid-loaded material 630 may be, or include, one or more primarily absorbent material. Absorption can be characterized as a bulk phenomena. An absorbent material typically releases volatile fluid more rapidly to the environment than an adsorbent material, so for non-limiting example, can provide a strong initial burst of air freshening. In contrast, an adsorbent material tends to exhibit slower release, and at a more sustained rate, of volatile fluid over a longer period of time. A workable absorbent material includes cellular foam, such as would be employed in manufacture of a cellulose or polymer sponge. Other workable absorbent materials include paper, such as cellulose paper or porous polymer paper, other porous polymer materials, foams made from polymers including polystyrene and polybutadiene, polystyrene-based and polybutadiene-based rubber, plastic of various compositions and configurations, and other absorbent materials, matted or arranged fibrous material, cotton, and the like. One workable polystyrene foam includes material used in the ubiquitous foam coffee cup. Desirably, the absorbent material is inert to the volatile fluid, or at least exhibits a benign reaction when the two are in contact.

A volatile fluid-loaded material 630 may include a mix of any suitable materials mentioned or suggested in this disclosure. Further, one or more such material may be carried in a matrix of other material, such as blended into a stream of plastic for injection molding. One or more additional beneficial agent may also be included, such as a selected commercially available enzymatic formulation for drain cleaning, or a gas-generating compound to promote transfer of volatile fluid vapor to the local environment. Several microbe-based enzymatic formulations are commercially available that are biodegradable. An exemplary gas-generating compound includes a metal carbonate with a solid acid, such as Calcium carbonate with citric acid. Moisture present in the local environment may be sufficient to generate gas from the gas-generating compound to facilitate, or enhance, delivery of volatile fluid vapor to that environment.

It has been found that powder made from a cellulose sponge can make a very desirable emanating structure. A commercially available cellulose sponge was soaked in water, frozen, and then crushed into a powder form in a blender. Remnant moisture in the thus-obtained and thawed foam powder may be removed prior to loading with a volatile fluid. For example, shredded or powdered foam may be dried by heating under vacuum for a period of time (e.g., 24 hours) at 60 to 80° C. The resulting absorbent foam powder, or meal, can be mixed with one or more adsorbent powder and a volatile fluid, like a fragrance, to make an emanating substance that resembles bread or cookie dough.

An exemplary emanating dough can be made according to the formula: 4 to 10 g cellulose foam powder; plus 10 to 30 g high surface area (>200 $m^2/g$) γ Alumina powder; plus 25 to 70 ml of fragrant oil. Sometimes a solvent, such as acetone, may be included in the mix, as well as one or more other material(s) to accomplish a particular objective.

Figure 53:
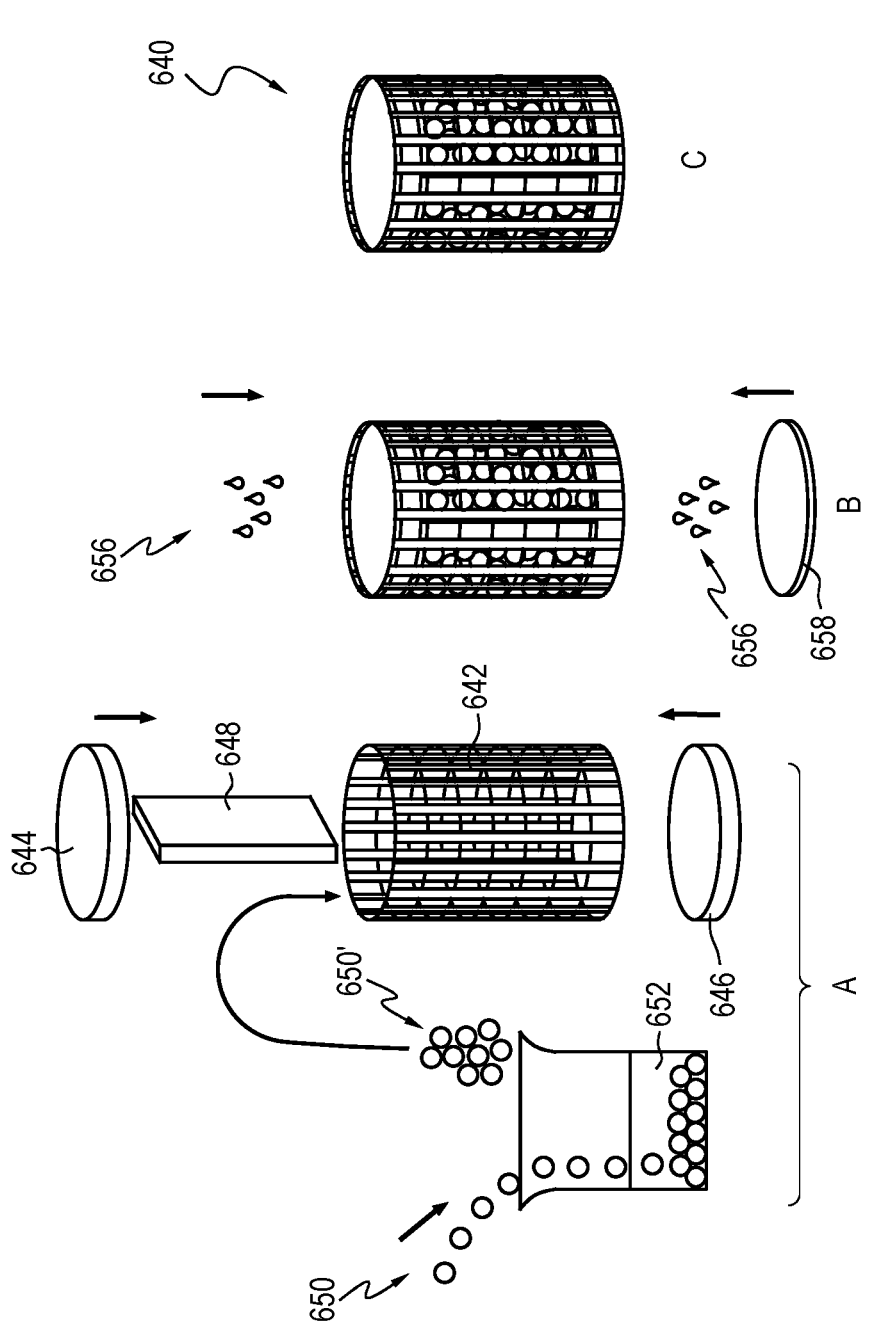
FIG. 53 illustrates assembly of an alternative emanating cartridge.

With reference now to FIG. 53, an exemplary emanator cartridge, generally indicated at 640, includes a cage 642, a top puck 644, a bottom puck 646, and a divider wall 648. Cage 642 provides a porous skeleton or framework to define a vented overall shape for the cartridge 640, and can be made from plastic, such as polypropylene. Alternative embodiments may include fewer or more constituent elements. For example, a workable embodiment may include only the skeleton, a quantity of beads, and a bottom cap, which may be plastic and/or sponge. Another embodiment may further include a top cap, which may be plastic and/or sponge. Another workable embodiment may include only the skeleton, a quantity of beads, and a dividing wall, which may be plastic and/or sponge.

As illustrated in FIG. 53, top puck 644 and bottom puck 646 are structured to fill the opposite end openings of the cage 642, and can act as cap elements. Wall 648 also spans across the cage and divides the cage 642 into compartments. In similar manner, additional walls may be provided to form additional compartments, if desired. It is currently preferred for one or more of pucks 644, 646 and wall 648 to be made from an absorbent material for rapid uptake and release of volatile fluid to the environment. An operable absorbent material includes a commercially available open-celled cellulose sponge, or other plastic or polymer sponge. When employed as an air freshener, the absorbent material provides a burst of fragrance to the environment upon deployment of the cartridge 640, and the adsorbent material provides a sustained product life. In a particular embodiment structured according to FIG. 53, 50 ml of fragrance was dispersed into the device; the top and bottom pucks were cellulose sponge material weighing about 1.5 g each, and the wall was a cellulose sponge weighing about 3 g, and the ¼ inch diameter Alumina beads weighed about 120 to 130 g.

During assembly, and indicated at A, a quantity of adsorbent material, generally 650, is preloaded with volatile fluid 652 by soaking the adsorbent elements 650 in a container 654 of volatile fluid 652. The bottom puck and wall 648 are installed in the cage 642 to define the compartments. The pre-loaded elements 650' are placed into the cage 642 to fill the compartments, and top puck 644 is installed. At B, a volatile fluid 656 is infused into one or more of the absorbent pucks 644, 646 and wall 648. An optional bottom cap 658 may be installed. A workable cap 658 may also be made from polypropylene. The completed cartridge 640 is illustrated at C. An exemplary adsorbent material may be selected from a material described above. The illustrated embodiment 640 includes Alumina elements 650 in spherical bead form, although other shapes of adsorbent material are also workable. It should be noted that volatile fluid 652 may be the same as volatile fluid 656, or different, in that a plurality of different fluids may be employed. For example, a blend of different scents may be desired in certain cases.

Figure 54:
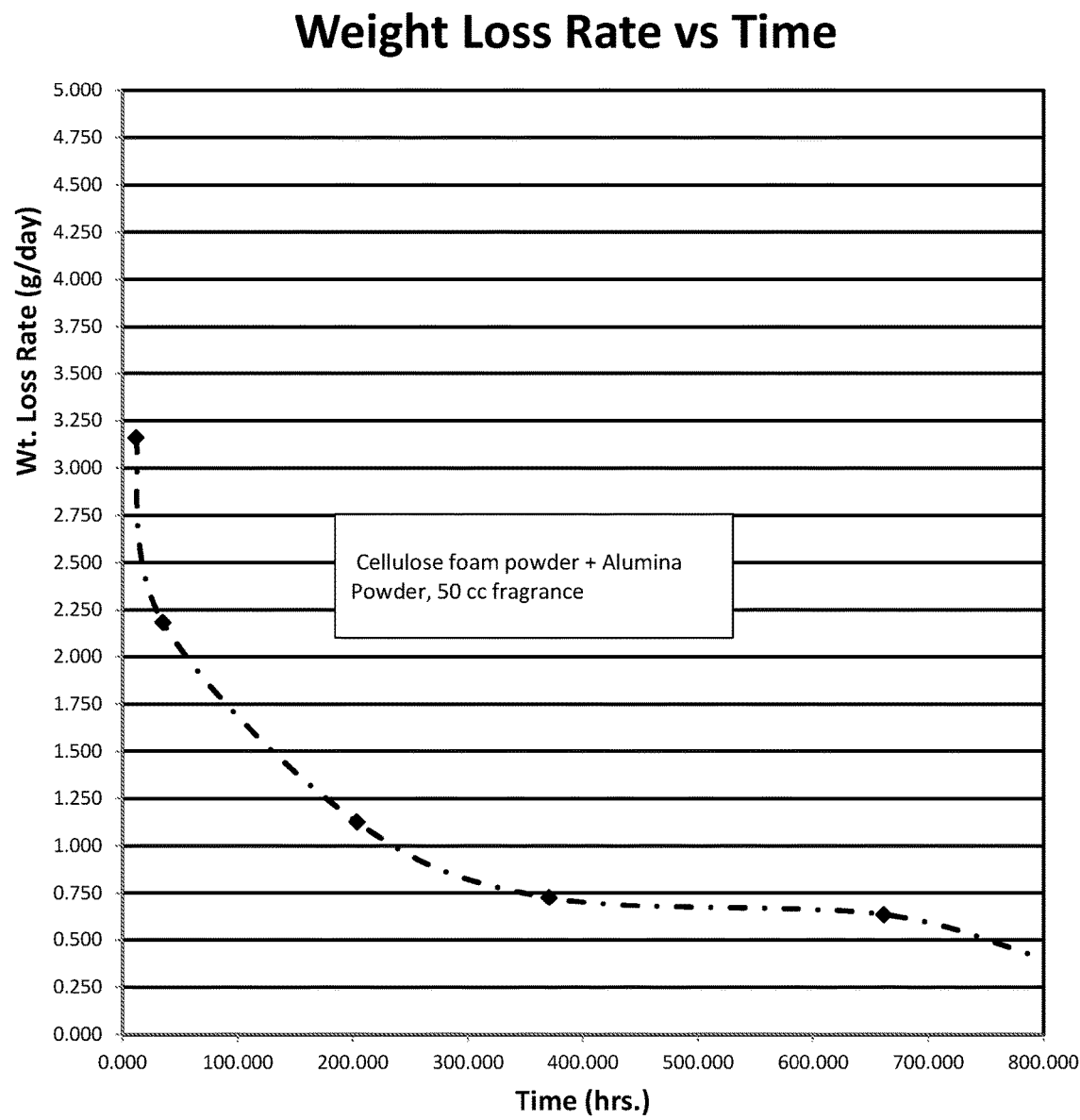
FIG. 54 is an X-Y plot showing release of volatile fluid over time by embodiments such as illustrated in FIG. 52.

FIG. 54 is an X-Y plot of the loss in weight of an emanator structured similar to the emanator 620 in FIG. 52. For the case illustrated in FIG. 54, the material 630 was made by blending 7.2 g cellulose foam powder and 16.8 g γ Alumina powder with 50 cc of fragrant oil. The Alumina and foam powder were first heat treated to remove moisture, then the fragrant oil was stirred into the combination of powders to form a dough. The dough was packed into a paper container, and covered with a top cover. Fragrant oil worked its way through, and evaporated into the local environment from the exterior of, the walls of the paper container. The weight of the thus-formed emanator was measured at intervals, and recorded in FIG. 54. The paper container operates as an emanator to disperse volatile vapor to the local environment.

Figure 55:
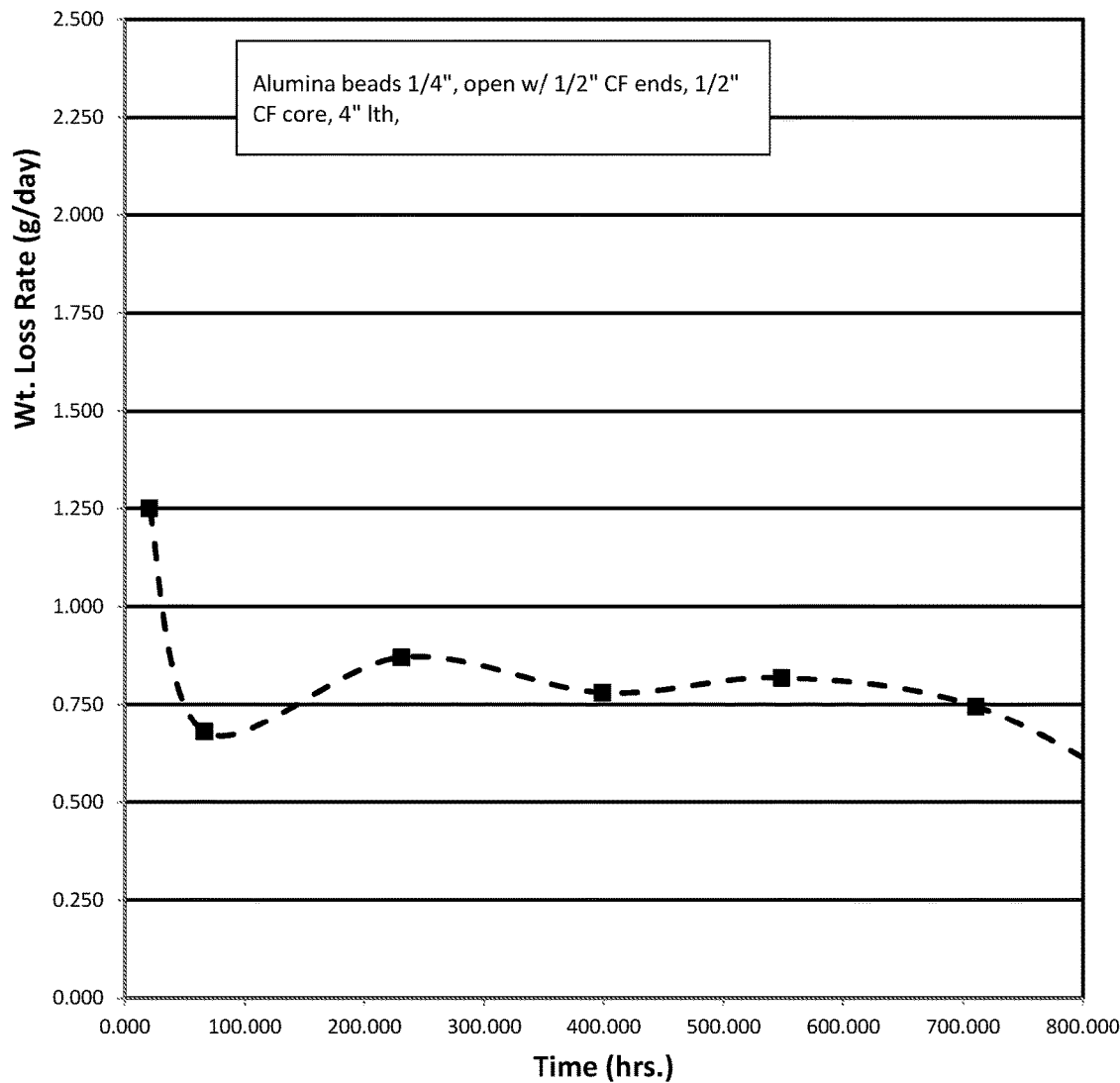
FIG. 55 is an X-Y plot showing release of volatile fluid over time by embodiments such as illustrated in FIG. 53.

A similar set of data is shown in FIG. 55, except that the emanator was structured similar to that illustrated in FIG. 53. For the case illustrated in FIG. 55, 78 g of Alumina beads having ¼ inch diameter were pre-loaded with 30 ml fragrant oil. It has been found that 100 g of Alumina beads will consistently adsorb about 40 g of fragrant oil. The wall and top and bottom pucks were made from ½ inch thick cellulose foam sponge material weighing in total 7 to 9 g, and the materials were loaded into a polypropylene screen/mesh tube having a 4 inch length, 2 inch diameter, and about 3/16 inch aperture size. A total of 20 ml of volatile fluid (a fragrant oil) was infused into the sponge materials. Weight of the thus-formed emanating cartridge was measured at intervals to generate FIG. 55.

Figure 56:
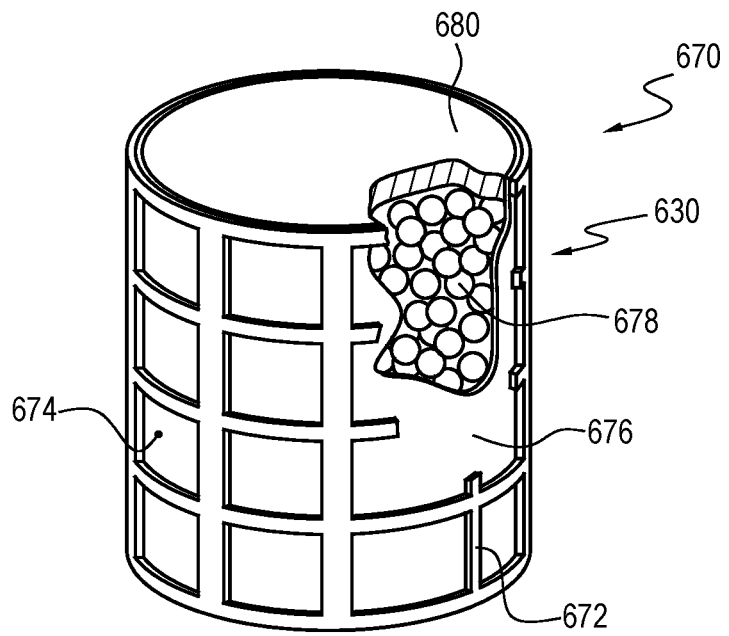
FIG. 56 is a side view in perspective of another embodiment.

Another emanating cartridge, generally indicated at 670, is illustrated in FIG. 56. Cartridge 670 includes a cage, or framework-like skeleton 672 that is structured to define a shape of the device 670. The skeleton 672 provides a plurality of vents, or windows 674, through which vapor may emanate into the local atmosphere. An emanator 676 may be provided to confine material 630 that is loaded with volatile fluid. Illustrated emanator 676 cooperates with skeleton 672 to define a shape for the cartridge 670, and can be made from any workable emanating material. Workable emanators 676 may be structured as a membrane, sack, bag, or more rigid element. Illustrated material 630 includes a plurality of small diameter adsorbent beads 678, which would pour through the illustrated windows 674 without additional restraint. Of course, when material 630 is structured to remain confined within the skeleton 672 on its own, an emanator 676 may not be required. Also, an optional cap 680 and floor (not illustrated) may be provided in a cartridge 670.

Figure 57:
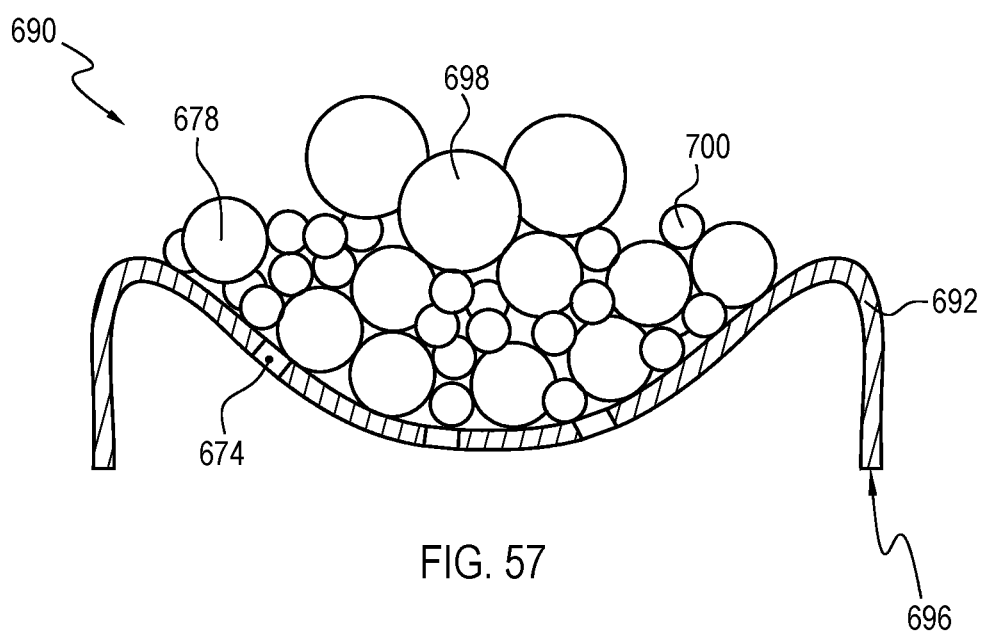
FIG. 57 is a cross-section view in elevation of another embodiment.

Another volatile fluid-emanating device, generally indicated at 690, is illustrated in cross-section in FIG. 57. Device 690 is particularly structured for use as a urinal air freshener, and includes a support dish 692 in which are confined a plurality of volatile fluid-holding adsorbent beads 678. Dish 692 includes a plurality of drain apertures 694, and may be structured to provide a support perimeter 696 as required to fit into any of a variety of urinals. It is within contemplation that an alternative embodiment may not include a support dish, and may simply include beads sized for direct application into a urinal bowl. Certain embodiments 690 may also include a drain cleaner (such as a plurality of cleaning beads 698) and a life-indicator (such as a plurality of color-changing beads 700).

The beads illustrated in FIG. 57 are sized on the order of about ¼ inch in diameter. Such beads have an inherent splash knock-down capability that is useful in a urinal application. FIG. 57 illustrates beads that are loose in the dish 692 and open to the local environment. However, it is within contemplation to also include a covering element of some sort over the beads, with the cover being structured to resist vandalism and bead scattering.

Sometimes, measures may be taken to retard release of fragrance or volatile vapor from an air freshening device. For example, a device disposed for service in repetitive or extended fluid flow may be undesirably depleted before the end of its intended service life, due to interaction with the flowing fluid in which the device is bathed. One way to retard depletion of volatile fluid is by providing a coating to the device, where the coating inherently slows down a rate of emanation of volatile fluid. A coating can operate to resist washing the volatile fluid from the carrier material, or reservoir, for the volatile fluid.

Figures 58, 59:
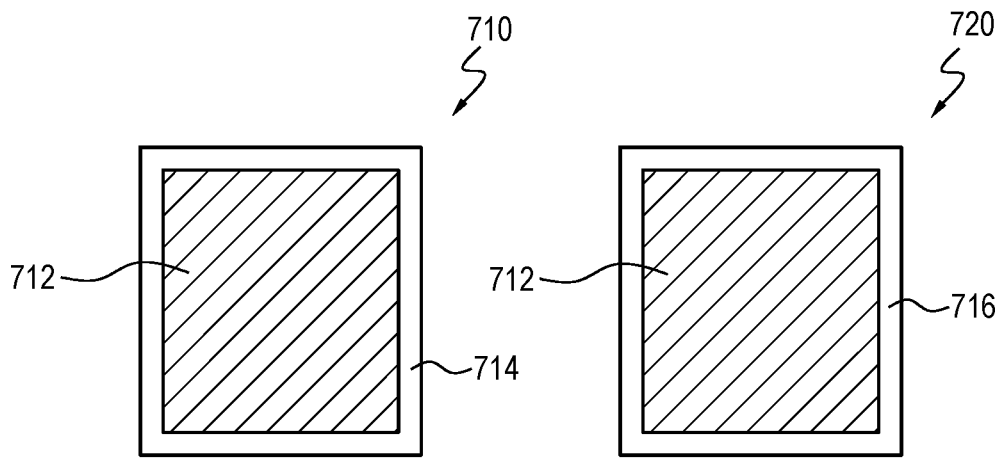
FIG. 58 is a cross-section view of another embodiment.
FIG. 59 is a cross-section view of another embodiment.

An exemplary embodiment of one such air freshening device for application in periodic, intermittent, or event steadily flowing water is generally indicated at 710 in FIG. 58. Device 710 includes an absorbent material 712 that is coated by a thin layer of retardant material 714, such as rubber or polymer. A volatile fluid is absorbed in the body of device 710. The coating permits emanation of vapor from the volatile fluid at a desired rate, but resists washing the volatile fluid away. An exemplary absorbent material 712 includes a cellulose sponge that is preloaded with fragrance prior to application of the coating 714. As one example, a relatively thin coating 714 of styrene-based, or butadiene-based rubber may be applied by spraying over the surface of an absorbent material 712 that has a desired shape and conformation. Similarly, a coating of ceramic having a high surface area 716 may be applied over the surface of an absorbent material, such as a fragrance-laden sponge 712, as illustrated by the embodiment generally indicated at 720 in FIG. 59.

Figures 60, 61:
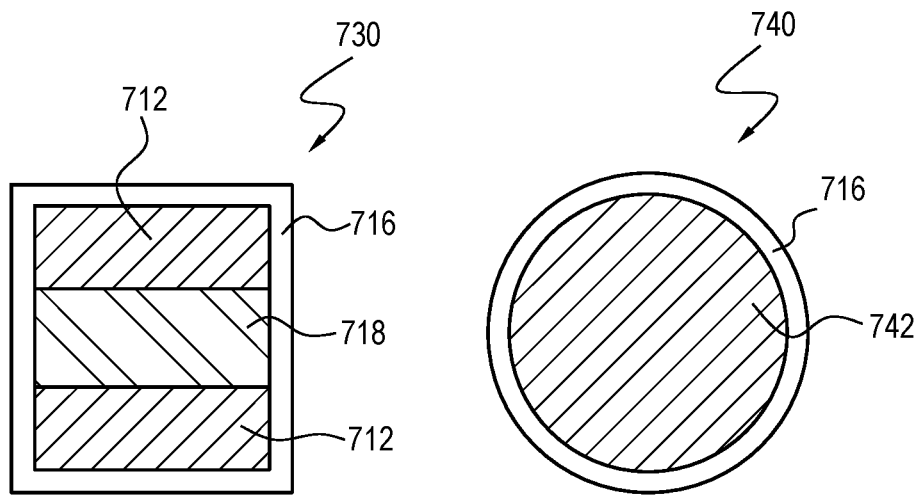
FIG. 60 is a cross-section view of another embodiment.
FIG. 61 is a cross-section view of another embodiment.

The embodiment generally indicated at 730 in FIG. 60 further includes a gas-generating material 718 to facilitate delivery of volatile vapor from the device 730. A balance may be made to regulate release of fragrant material vapors to the environment by the combination and proportions of the coating 716 and the gas-generating material 718. In such case, a coating 716 is structured and arranged to permit moisture to pass into the device at a slow rate, and volatile vapor to exit the device 730 at a corresponding desired rate. It is within contemplation that the gas-generating material 718 may be mixed into, or distributed throughout the adsorbent material, rather than formed as the separate portion as illustrated. Further, an adsorbent material (not illustrated in FIG. 60) may also be included in certain embodiments.

The embodiment indicated generally at 740 in FIG. 61 includes a volatile fluid-loaded adsorbent material 742 that is covered with a thin coating 716. A currently preferred adsorbent material 742 includes high-surface area ceramic such as Alumina in bead form. Other adsorbent materials disclosed above are also workable. A workable coating includes rubber or polymeric coatings. A workable coating 716 may be formulated and configured (e.g., in thickness), to provide a desired degree of water resistance as an operable mechanism to control a rate of emanation into the local environment vs. protection of the volatile fluid from rapid depletion. A coating may operate to reduce a rate of evaporation of volatile fluid from the reservoir material that hold a quantity of volatile fluid for an emanator. A coating may also reduce a rate at which water molecules migrate into the reservoir material.

An alternative release-rate control mechanism (not illustrated) includes adsorbing one or more rate-controlling element into an adsorbent material, along with one or more volatile fluid. For example, one exemplary embodiment was made by combining a solution formed by the combination of 25 g fragrant oil with 5 g of Styrofoam (from a foam coffee cup) and 1 cc of acetone with 90 g of high-surface area Alumina beads having a diameter of about ¼ inch. The solution was completely taken up by the beads in 24 to 72 hours, and resulted in beads that exhibited sustained release of fragrance over an extended period of time in both a watery and dry air environment.

Figure 62:
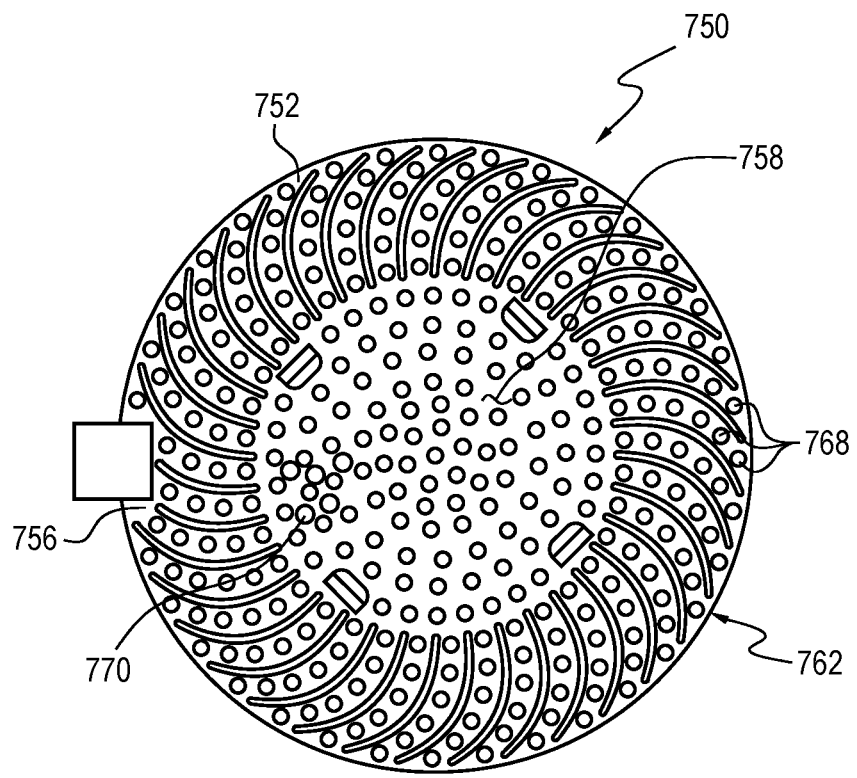
FIG. 62 is a top plan view of an alternative embodiment.
Figure 63:
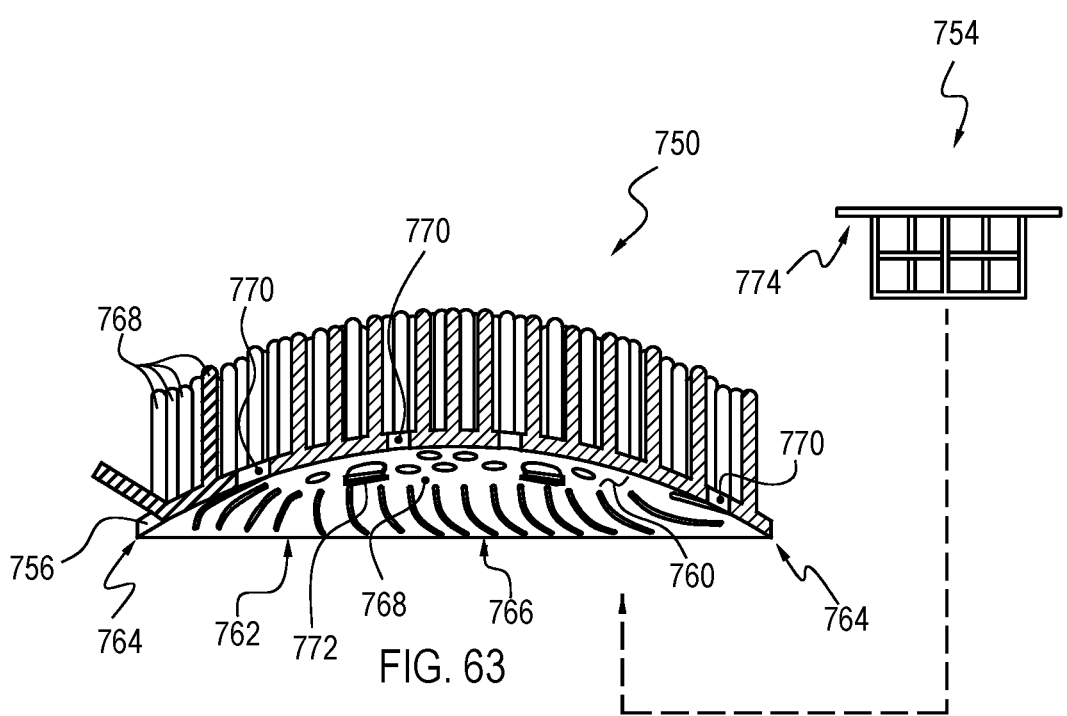
FIG. 63 is a cross-section view through a midline of the embodiment in FIG. 62.

Another embodiment of an air freshener is indicated generally at 750 in FIGS. 62 and 63. Air freshener 750 is particularly adapted for use as a urinal screen, and includes an emanator portion 752, and a container, generally 754. Emanator 752 is formed from a material capable of imbibing a volatile fluid when exposed to the volatile fluid in a liquid environment and subsequently off-gassing the imbibed volatile fluid when exposed to a gas or vapor phase environment. As mentioned above, a workable substrate material for forming an emanator includes styrene-based polymer, styrene-based rubber, ethylene propylene diene monomer (EPDM), thermoplastic polyurethane (TPU), butadiene-based polymer, butadiene-based rubber, gum rubber, and cellulosic rubber, among other options.

It is currently preferred for an emanator 750 to be structured as a unitary element, as illustrated in e.g., FIGS. 62 and 63. It is currently preferred to manufacture that emanator by way of an injection molding process. Embodiments may essentially be "stand alone" elements that may be used as air fresheners in their own right. An emanator 750 is typically first formed in a desired "final-form" structural configuration, and that final-form structure is then loaded with a volatile fluid at ambient temperature conditions. It is to be understood that extensive imbibing of volatile fluid may cause certain substrates to "swell" slightly as the volatile fluid is imbibed. For certain embodiments 750, the emanator may be structured to resist a humanly perceptible change in configuration size and shape from the final-form during a useful life of the emanator for air freshening.

Emanator 750 includes a shell 756 with a top surface 758 spaced apart from a bottom surface 760 by a substantially uniform distance or thickness. A rim 762 of the shell 756 provides a support foot, generally 764, disposed around a portion of a perimeter 766 of the shell 756 to support the shell 756 on a surface during use. A cross-section of the shell 756 may possess an arcuate shape to define a volume 768 bounded in part by the bottom surface 760 and being open to permit access to the volume through an opening bounded by the perimeter 766. Desirably, the top surface 758 carries a plurality of upstanding splash knock-down structures 768, and the shell 756 includes a plurality of penetrations 770 structured to permit fluid to travel through the shell 756.

Preferably, bottom surface 760 is structured to permit attachment of a container 754 there-to. As illustrated, a workable container 754 is porous to permit travel of fluid there-through. Also as illustrated, container 754 is structured in harmony with the emanator 752 to permit the container 754 to be installed in registration with the emanator 752 in a tool-free operation. In certain cases, and as illustrated, the shell 756 is transversely flexible and may be deformed to permit engagement of the container 754 to the shell's coupling devices. In FIG. 63, a plurality of coupling hooks 772 carried by emanator 752 are configured to engage a rim, generally 774, of the container to hold container 754 in installed registration. A container 754 may also be structured in harmony with the emanator 752 to permit the container 754 to be removed from registration with the emanator 752 in a tool-free operation to permit recharging the container with, for example, drain cleaning compound. Alternative coupling arrangements are within contemplation, including ubiquitous cooperating threaded structures, bayonet structures, other interlocking structures, and the like, carried by respective elements.

The invention may be embodied in a method for making an air freshener. One exemplary method includes providing an emanator in final-form, and configured as described above. A workable emanator may include one or more elements described with reference to any of the aforementioned embodiments. A workable emanator may be injection molded. Preferably, the emanator is structured to resist a humanly perceptible change in configuration size and shape from the final-form during a useful life of the emanator for air freshening. The method further includes wetting the emanator with a volatile fluid under ambient temperature conditions for between about 1 hour and about 48 hours to disperse a fragrant oil into the emanator to a weight percent of greater than about 3%, where weight percent is calculated as $A/B*100$, and A is weight of imbibed volatile fluid and B is weight of the emanator material prior to the imbibing process.

A method may further include attaching a container to depend from the bottom surface. A workable container is porous to permit travel of fluid there-through. A method may further include placing a first quantity of drain cleaning compound into the container prior to attaching the container to the bottom surface. One workable drain cleaning compound is enzyme-based, and slowly dissolves in a moist (e.g., wet) environment.

It is desirable for the container to be structured in harmony with the emanator to permit the container to be installed in registration with the emanator in a tool-free operation. A method may further include installing the container in registration with the bottom surface prior to placing the emanator in service to freshen air. It is also desirable for the container to be structured in harmony with the emanator to permit the container to be removed from registration with the emanator in a tool-free operation. A method may further include removing the container from registration with the bottom surface, refilling the container with a quantity of drain cleaning compound, and re-installing the container in registration with the bottom surface prior to again placing the emanator in service to freshen air.

Workable materials to form an emanator may be characterized by certain properties to distinguish over other materials. For example, one preferred emanator has a theoretical density of greater than 90%. As is well-known, theoretical density is the maximum achievable density of a particular element, compound, or alloy, assuming no internal voids or contaminants. It is calculated from the number of atoms per unit cell and measurement of the lattice parameters.

It is also preferred to structure an emanator from materials that have a melting point, or otherwise inherently avoid conglomeration or change from a final-form size and configuration, at a temperature above at least about 250° F. Sometimes, an emanator may have an inherent melting point above 300° F., 400° F., 500° F., or sometimes 1000° F., and even above 2000° C. in certain cases.

For purpose of this application, what is meant by "the emanator being structured to resist a humanly perceptible change in configuration size and shape from a final-form during a useful life of the emanator for air freshening", is intended to recognize that an emanator may swell slightly during an imbibing process, and substantially reverse that during an off-gas process. However, a human that is unaided by tools (such as a micrometer, caliper, ruler, or other measuring device) cannot detect that change. In contrast, conglomeration of a plurality of elements at elevated temperature to form a combination element is distinctly perceptible by an unaided human.

A self-supplied emanator is desirably capable of being internally loaded with volatile fluid at substantially ambient temperature conditions, and then autonomously off-gassing the volatile fluid in vapor phase into a vapor phase local environment. That low-temperature loading provides cost-effective manufacturing use of relatively expensive volatile fluid (e.g., various scents and scented oils). During the loading process, the emanator may be characterized as imbibing or up-taking the volatile fluid. The imbibing process may take one or more of several mechanisms or forms, including absorption, adsorption, diffusion, and molecular disruption, combination, or reaction, depending upon material composition of the emanator substrate and the selected volatile fluid(s). Each such imbibing or fluid transfer mechanism to load or infuse volatile fluid into an emanator substrate is properly regarded as functioning under a unique and separately distinguishable principle of operation.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. It will be appreciated by one of ordinary skill that certain embodiments, such as above-described urinal air fresheners, may be modified for alternative application, such as for operation in an automobile, closet, or clothes drier, for non-limiting examples. Elements described with reference to one embodiment may sometimes be extracted for separate use, or in combination with one or more elements from the same or a different embodiment. All changes which come within the meaning and range of equivalency of the claims are to be embraced within their scope.

What is claimed is:

1. A method for making an air freshener, comprising:
providing an emanator in final-form, the emanator being structured to resist a humanly perceptible change in configuration size and shape from said final-form during a useful life of the emanator for air freshening, the emanator being formed from a material capable of imbibing a volatile fluid when exposed to the volatile fluid in a liquid environment and subsequently off-gassing the imbibed volatile fluid when exposed to a gas environment; and
wetting the emanator with a volatile fluid under ambient temperature conditions for between about 1 hour and about 48 hours to disperse a fragrant oil into the emanator to a weight percent of greater than about 3%, where weight percent is calculated as A/B*100, and A is weight of imbibed volatile fluid and B is weight of the emanator material prior to the imbibing process.

2. The method according to claim 1, wherein:
the emanator is structured as a unitary element from a material selected from the group consisting of styrene-based polymer, styrene-based rubber, thermoplastic polyurethane (TPU), butadiene-based polymer, butadiene-based rubber, gum rubber, and cellulosic rubber.

3. The method according to claim 1, wherein:
the emanator is structured as a unitary element from a material selected from the group consisting of styrene-based rubber, thermoplastic polyurethane (TPU), butadiene-based rubber, and cellulosic rubber.

4. The method according to claim 1, wherein:
the entire emanator is injection molded as a single unitary element.

5. The method according to claim 1, wherein:
the emanator comprises a shell with a top surface spaced apart from a bottom surface by a substantially uniform distance, a rim of the shell providing a support foot disposed around a portion of a perimeter of the shell to support the shell on a surface during use, a cross-section of the shell having an arcuate shape to define a volume bounded in part by the bottom surface and being open to permit access to the volume through an opening bounded by the perimeter, the top surface carrying a plurality of upstanding splash knock-down structures, the shell having a plurality of penetrations structured to permit fluid to travel through the shell.

6. The method according to claim 5, wherein:
the bottom surface is structured to permit attachment of a container there-to; and further comprising:
attaching a container to depend from the bottom surface.

7. The method according to claim 6, wherein:
the container is porous to permit travel of fluid therethrough, and further comprising:
placing a first quantity of enzyme-based drain cleaning compound into the container prior to attaching the container to the bottom surface.

8. The method according to claim 6, wherein:
the container is structured in harmony with the emanator to permit the container to be installed in registration with the emanator in a tool-free operation, and further comprising:
installing the container in registration with the bottom surface prior to placing the emanator in service to freshen air.

9. The method according to claim 8, wherein:
the container is structured in harmony with the emanator to permit the container to be removed from registration with the emanator in a tool-free operation, and further comprising:
removing the container from registration with the bottom surface;
refilling the container with a quantity of drain cleaning compound; and
re-installing the container in registration with the bottom surface prior to placing the emanator in service to freshen air.

10. The method according to claim 1, wherein:
the emanator has a theoretical density of greater than 90%.

11. An apparatus, comprising:
an emanator structured to resist a humanly perceptible change in configuration size and shape during a useful life of the emanator for air freshening, the emanator being formed from a material capable of imbibing a volatile fluid when exposed to the volatile fluid in a liquid environment and subsequently off-gassing the imbibed volatile fluid when exposed to a gas environment; and a volatile fluid dispersed into the emanator to a weight percent of between about 3% and about 300%, where weight percent is calculated as A/B*100, and A is weight of the volatile fluid and B is dry weight of the emanator.

12. The apparatus according to claim 11, wherein:
the emanator is structured as a unitary element from a material selected from the group consisting of styrene-based polymer, styrene-based rubber, thermoplastic polyurethane (TPU), butadiene-based polymer, butadiene-based rubber, gum rubber, and cellulosic rubber.

13. The apparatus according to claim 11, wherein:
the emanator is structured as a unitary element from a material selected from the group consisting of styrene-based rubber, thermoplastic polyurethane (TPU), butadiene-based rubber, and cellulosic rubber.

14. The apparatus according to claim 11, wherein:
the entire emanator is injection molded as a single unitary element.

15. The apparatus according to claim 11, wherein:
the emanator comprises a shell with a top surface spaced apart from a bottom surface by a substantially uniform thickness, a rim of the shell providing a support foot disposed around a portion of a perimeter of the shell to support the shell on a surface during use, the shell having a concave shape to define a volume bounded in part by the bottom surface and being open to permit access to the volume through an opening bounded by the perimeter, the top surface carrying a plurality of upstanding splash knock-down structures, the shell having a plurality of apertures structured to permit fluid travel through the shell thickness.

16. The apparatus according to claim 15, wherein:
the bottom surface is structured to permit attachment of a container there-to.

17. The apparatus according to claim 16, further comprising:
a porous container structured to permit travel of fluid there-through; and
a first quantity of dissolvable enzyme-based drain cleaning compound disposed in the container and in a path of fluid flow from at least one of the apertures.

18. The apparatus according to claim 17, wherein:
the container is structured in harmony with the emanator to permit the container to be installed in registration with the emanator in a tool-free operation.

19. The apparatus according to claim 18, wherein:
the container is structured in harmony with the emanator to permit the container to be removed from registration with the emanator in a tool-free operation to permit refilling the container with drain cleaning compound.

20. The apparatus according to claim 11, wherein:
the emanator has a theoretical density of greater than 90%.

* * * * *